United States Patent [19]
Petersen et al.

[11] Patent Number: 5,990,122
[45] Date of Patent: Nov. 23, 1999

[54] QUINOLONE- AND NAPHTHYRIDONECARBOXYLIC ACID DERIVATIVES

[75] Inventors: Uwe Petersen, Leverkusen; Thomas Schenke, Bergisch Gladbach; Thomas Jaetsch, Köln; Stephan Bartel, Bergisch Gladbach; Klaus Dieter Bremm, Recklinghausen; Rainer Endermann; Karl Georg Metzger, both of Wuppertal, all of Germany

[73] Assignee: Bayer Aktiengesellschaft, Leverkusen, Germany

[21] Appl. No.: 09/003,613

[22] Filed: Jan. 7, 1998

Related U.S. Application Data

[62] Division of application No. 08/764,548, Dec. 12, 1996, Pat. No. 5,753,669, which is a division of application No. 08/508,603, Jul. 28, 1995, Pat. No. 5,605,910.

[30] Foreign Application Priority Data

Aug. 4, 1994 [DE] Germany ............... 44 27 530

[51] Int. Cl.$^6$ .......... A61K 31/40; A61K 31/47; C07D 215/233; C07D 221/02
[52] U.S. Cl. ............ 514/294; 514/229.2; 514/230.2; 514/224.5; 544/66; 544/32; 544/101; 546/94
[58] Field of Search ............... 546/94; 544/66, 544/101, 32; 514/294, 229.2, 230.2, 224.5

[56] References Cited

U.S. PATENT DOCUMENTS

| | | | |
|---|---|---|---|
| 4,864,023 | 9/1989 | Yokose | 544/66 |
| 4,988,709 | 1/1991 | Ogata | 514/314 |
| 5,026,856 | 6/1991 | Yatsunami | 546/156 |
| 5,312,823 | 5/1994 | Petersen | 514/300 |
| 5,457,104 | 10/1995 | Bartel | 514/234.5 |
| 5,578,604 | 11/1996 | Himmler | 514/312 |
| 5,585,491 | 12/1996 | Domagala | 546/123 |
| 5,631,256 | 5/1997 | Demuth | 514/252 |
| 5,631,266 | 5/1997 | Kim | 514/300 |
| 5,679,675 | 10/1997 | Jaetsch | 514/229.2 |

FOREIGN PATENT DOCUMENTS

| | | |
|---|---|---|
| 0 429 304 | 5/1989 | European Pat. Off. . |
| 429304 | 5/1989 | European Pat. Off. . |
| 0 343 524 | 11/1989 | European Pat. Off. . |
| 343524 | 11/1989 | European Pat. Off. . |
| 0 387 802 | 9/1990 | European Pat. Off. . |
| 387802 | 9/1990 | European Pat. Off. . |
| 0 520 240 | 12/1992 | European Pat. Off. . |
| 520240 | 12/1992 | European Pat. Off. . |
| 0 523 512 | 1/1993 | European Pat. Off. . |
| 523512 | 1/1993 | European Pat. Off. . |
| 0 607 825 | 7/1994 | European Pat. Off. . |
| 607825 | 7/1994 | European Pat. Off. . |
| 0 647 644 | 4/1995 | European Pat. Off. . |
| 647644 | 4/1995 | European Pat. Off. . |
| 0 671 391 | 9/1995 | European Pat. Off. . |
| 671391 | 9/1995 | European Pat. Off. . |
| 4 230 804 | 3/1994 | Germany . |
| 9 212 146 | 7/1992 | WIPO . |

OTHER PUBLICATIONS

Derwert Abstract of JP 04–253 973, (Sep. 9, 1992).

*Primary Examiner*—D. Margaret M. Mach
*Attorney, Agent, or Firm*—Sprung Kramer Schaefer & Briscoe

[57] ABSTRACT

The invention relates to new quinolone- and naphthyridonecarboxylic acid derivatives which are substituted in the 7-position by a tricyclic amine radical, their salts, processes for their preparation and antibacterial compositions comprising these compounds.

9 Claims, No Drawings

QUINOLONE- AND NAPHTHYRIDONECARBOXYLIC ACID DERIVATIVES

This is a division of application Ser. No. 08/764,548, filed Dec. 12, 1996, now U.S. Pat. No. 5,753,669 which is a division of application Ser. No. 08/508,603, filed Jul. 28, 1995, now U.S. Pat. No. 5,605,910.

The invention relates to new quinolone- and naphthyridonecarboxylic acid derivatives which are substituted in the 7-position by a tricyclic amine radical, their salts, processes for their preparation and antibacterial compositions comprising these compounds.

Quinolonecarboxylic acids which are substituted in the 7-position by a bicyclic unsaturated amine radical are already known from the patent applications EP 520 240 (Bayer) and JP 4 253 973 (Banyu). These compounds are distinguished by a high antibacterial activity. However, they have the disadvantage that they have a high genotoxic potential, which renders their use as medicaments impossible. The invention is therefore based on the object of discovering compounds which show a reduction in genotoxic properties, coupled with a high antibacterial activity.

It has now been found that the compounds of the formula (I)

in which

Q denotes a radical of the formulae

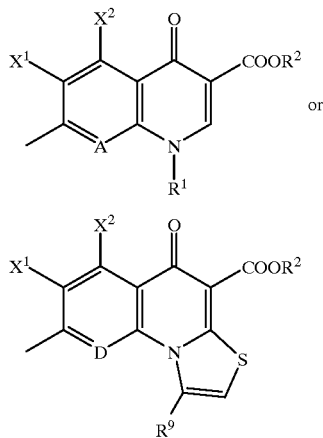

wherein
$R^1$ represents alkyl which has 1 to 4 carbon atoms and is optionally mono- or disubstituted by halogen or hydroxyl, alkenyl having 2 to 4 carbon atoms, cycloalkyl which has 3 to 6 carbon atoms and is optionally substituted by 1 or 2 fluorine atoms, bicyclo[1.1.1]-pent-1-yl, 1,1-dimethylpropargyl, 3-oxetanyl, methoxy, amino, methylamino, dimethylamino or phenyl which is optionally mono- or disubstituted by halogen, amino or hydroxyl,
$R^2$ represents hydrogen, alkyl which has 1 to 3 carbon atoms and is optionally substituted by hydroxyl, methoxy, amino or dimethylamino, benzyl, (5-methyl-2-oxo-1,3-dioxol-4-yl)-methyl, acetoxymethyl, pivaloyloxymethyl, 5-indanyl, phthalindinyl or 3-acetoxy-2-oxo-butyl,
$R^9$ represents hydrogen or alkyl which has 1 to 3 carbon atoms and is optionally substituted by methoxy, hydroxyl or halogen,
$X^1$ represents halogen or nitro,
$X^2$ represents hydrogen, halogen, amino, hydroxyl, methoxy, mercapto, methyl, halogenomethyl or vinyl,
A represents N or C—$R^7$, wherein
$R^7$ represents hydrogen, halogen, $CF_3$, $OCH_3$, $OCHF_2$, $CH_3$, CN, $CH=CH_2$ or $C\equiv CH$, or together with $R^1$ can also form a bridge having the structure —*O—$CH_2$—CH—$CH_3$, —*S—$CH_2$—$CH_2$—, —*S—$CH_2$—CH—$CH_3$, —*S—$CH_2$—CH—$CH_2F$, —*$CH_2$—$CH_2$—CH—$CH_3$ or —*O—$CH_2$—N—$R^8$, wherein the atom labelled with * is linked to the carbon atoms of A and wherein
$R^8$ denotes hydrogen, methyl or formyl, and
D represents N or C—$R^{10}$, wherein
$R^{10}$ represents hydrogen, halogen, $CF_3$, $OCH_3$, $OCHF_2$ or $CH_3$, or together with $R^9$ can also form a bridge having the structure —*O—$CH_2$—, —*NH—$CH_2$—, —*N($CH_3$)—$CH_2$—, —*N($C_2H_5$)—$CH_2$—, —*N($C_3H_5$)—$CH_2$— or —*S—$CH_2$—, wherein the atom labelled with * is linked to the carbon atom of D, and T denotes a radical of the formula

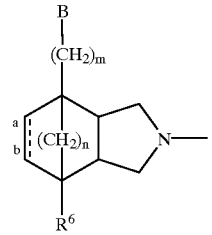

wherein
B represents $NR^3R^4$ or $OR^5$, wherein
$R^3$ represents hydrogen, methyl or alkoxycarbonyl having 1 to 4 carbon atoms in the alkyl part,
$R^4$ represents hydrogen or methyl and
$R^5$ represents hydrogen or methyl,
$R^6$ represents hydrogen or methyl,
m represents 0 or 1 and
n represents 1 or 2, and wherein a single or a double bond can stand between the carbon atoms a and b, and pharmaceutically usable hydrates and acid addition salts thereof, as well as the alkali metal, alkaline earth metal, silver and guanidinium salts of the underlying carboxylic acids, have a high antibacterial action, in particular against Gram-positive bacteria, coupled with a good tolerability.

Preferred compounds of the formula (I) are those in which

Q and T have the abovementioned meaning and
$R^1$ represents alkyl which has 1 to 4 carbon atoms and is optionally mono- or disubstituted by halogen, alkenyl having 2 to 3 carbon atoms, cycloalkyl which has 3 or 4 carbon atoms and is optionally substituted by 1 fluorine atom, bicyclo[1.1.1]pent-1-yl, 1,1-dimethylpropargyl, 3-oxetanyl, methylamino or phenyl which is optionally mono- or disubstituted by fluorine, amino or hydroxyl,
$R^2$ represents hydrogen, alkyl having 1 to 2 carbon atoms, benzyl or (5-methyl-2-oxo-1,3-dioxol-4-yl)-methyl,
$R^9$ represents hydrogen or alkyl which has 1 to 2 carbon atoms and is optionally mono- to trisubstituted by fluorine, $X^1$ represents fluorine or chlorine, $X^2$ represents hydrogen, halogen, amino, methyl, trifluoromethyl or vinyl, A represents N or C—$R^7$, wherein
$R^7$ represents hydrogen, halogen, $CF_3$, $OCH_3$, $OCHF_2$, $CH_3$, CN, CH=$CH_2$ or C≡CH, or together with $R^1$ can also form a bridge having the structure —*O—$CH_2$—CH—$CH_3$, —*S—$CH_2$—$CH_2$—, —*$CH_2$—$CH_2$—CH—$CH_3$ or —*O—$CH_2$—N—$R^8$, wherein the atom labelled with * is linked to the carbon atom of A, and wherein
$R^8$ denotes hydrogen or methyl, and D represents N or C—$R^{10}$, wherein
$R^{10}$ represents hydrogen, fluorine, chlorine, $CF_3$, $OCH_3$ or $CH_3$, or together with $R^9$ can also form a bridge having the structure —O—$CH_2$—, —*N($CH_3$)—$CH_2$—, —*N($C_2H_5$)—$CH_2$—, —*N($C_3H_5$)—$CH_2$— or —*S—$CH_2$—, wherein the atom labelled with * is linked to the carbon atom of D, and B represents $NR^3R^4$ or $OR^5$, wherein
$R^3$ represents hydrogen, methyl or alkoxycarbonyl having 1 to 4 carbon atoms in the alkyl part,
$R^4$ represents hydrogen or methyl and
$R^5$ represents hydrogen or methyl, $R^6$ represents hydrogen or methyl, m represents 0 or 1 and n represents 1 or 2, wherein a single or a double bond can stand between the carbon atoms a and b, and pharmaceutically usable hydrates and acid addition salts thereof and the alkali metal, alkaline earth metal, silver and guanidinium salts of the underlying carboxylic acids.

Compounds of the formula (I) which are particularly preferred are those
in which
Q and T have the abovementioned meaning and
in which
$R^1$ represents alkyl which has 1 to 4 carbon atoms and is optionally mono- or disubstituted by fluorine, vinyl, cyclopropyl which is optionally substituted by 1 fluorine atom or phenyl which is optionally mono- or disubstituted by fluorine,
$R^2$ represents hydrogen, alkyl having 1 to 2 carbon atoms or (5-methyl-2-oxo-1,3-dioxol-4-yl)-methyl,
$R^9$ represents hydrogen or methyl which is optionally mono- to trisubstituted by fluorine,
$X^1$ represents fluorine,
$X^2$ represents hydrogen, fluorine, amino, methyl or vinyl,
A represents N or C—$R^7$, wherein
$R^7$ represents hydrogen, fluorine, chlorine, bromine, $CF_3$, $OCH_3$, $OCHF_2$, $CH_3$, CN, CH=$CH_2$ or C≡CH, or together with $R^1$ can also form a bridge having the structure —*O—$CH_2$—CH—$CH_3$ or —*O—$CH_2$—N—$R^8$, where the atom labelled with * is linked to the carbon atom of A, and wherein
$R^8$ denotes hydrogen or methyl, and D represents N or C—$R^{10}$, wherein
$R^{10}$ represents hydrogen, fluorine, chlorine or $OCH_3$, or together with $R^9$ can also form a bridge having the structure —*O—$CH_2$—, —*N($CH_3$)—$CH_2$—, —*N($C_2H_5$)—$CH_2$— or —*S—$CH_2$—, wherein the atom labelled with * is linked to the carbon atom of D, and B represents $NR^3R^4$ or $OR^5$, wherein
$R^3$ represents hydrogen or methyl,
$R^4$ represents hydrogen or methyl and
$R^5$ represents hydrogen or methyl, $R^6$ represents hydrogen, m represents 0 or 1 and n represents 1 or 2, wherein a single or a double bond can stand between the carbon atoms a and b, and pharmaceutically usable hydrates and acid addition salts thereof and the alkali metal, alkaline earth metal, silver and guanidinium salts of the underlying carboxylic acids.

It has furthermore been found that the compounds of the formula (I) are obtained by a process in which compounds of the formula (II)

$$Y—Q \qquad (II)$$

in which

Q has the abovementioned meaning and

Y represents halogen, in particular fluorine or chlorine, are reacted with compounds of the formula (III)

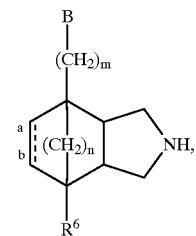

(III)

in which

B, $R^6$, m, n, a and b have the abovementioned meanings, if appropriate in the presence of acid-trapping agents, and any protective groups are split off.

If, for example, 6,7-difluoro-1-cyclopropyl-1,4-dihydro-8-methoxy-4-oxo-3-quinolinecarboxylic acid and 4-azatricyclo[5.2.1.0^{2,6}]dec-8-en-1-ylamine are used as starting substances, the course of the reaction can be represented by the following equation:

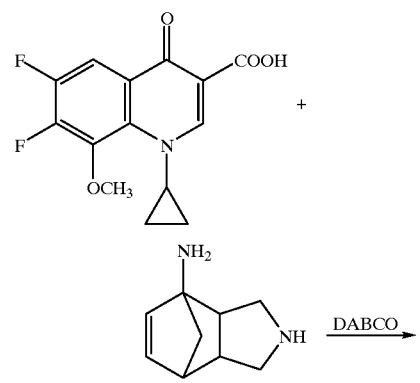

-continued

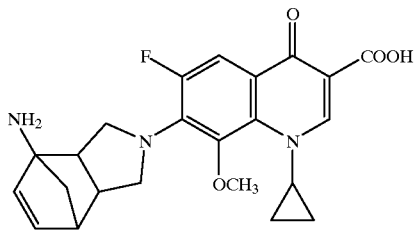

The compounds of the formula (II) used as starting compounds are known or can be prepared by known methods. They can be employed either as racemic or as enantiomerically pure compounds. Examples which may be mentioned are 7-chloro-1-cyclopropyl-6-fluoro-1,4-dihydro-4-oxo-3-quinolinecarboxylic acid, 1-cyclopropyl-6,7-difluoro-1,4-dihydro-4-oxo-3-quinolinecarboxylic acid, 6-chloro-1-cyclopropyl-7,8-difluoro-1,4-dihydro-4-oxo-3-quinolinecarboxylic acid, 8-chloro-1-cyclopropyl-6,7-difluoro-1,4-dihydro-4-oxo-3-quinolinecarboxylic acid, 1-cyclopropyl-6,7,8-trifluoro-1,4-dihydro-4-oxo-3-quinolinecarboxylic acid, 5-bromo-1-cyclopropyl-6,7,8-trifluoro-1,4-dihydro-4-oxo-3-quinolinecarboxylic acid, 5-bromo-1-(2,4-difluorophenyl)-6,7,8-trifluoro-1,4-dihydro-4-oxo-3-quinolinecarboxylic acid, 1-cyclopropyl-6,7-difluoro-1,4-dihydro-8-methyl-4-oxo-3-quinolinecarboxylic acid, 6,7-difluoro-1-ethyl-1,4-dihydro-4-oxo-3-quinolinecarboxylic acid, 7-chloro-6-fluoro-1-ethyl-1,4-dihydro-4-oxo-3-quinolinecarboxylic acid, 7-chloro-6-fluoro-1,4-dihydro-1-(2-hydroxyethyl)-4-oxo-3-quinolinecarboxylic acid, 6,7-difluoro-1-(2-fluoroethyl)-1,4dihydro-4-oxo-3-quinoline-carboxylic acid, 7-chloro-6-fluoro-1,4-dihydro-1-methoxy-4-oxo-3-quinolinecarboxylic acid, 7-chloro-6-fluoro-1,4-dihydro-1-methylamino-4-oxo-3-quinolinecarboxylic acid, 6,7-difluoro-1,4-dihydro-4-oxo-1-phenyl-3-quinolinecarboxylic acid, 7-chloro-1-cyclopropyl-6-fluoro-1,4-dihydro-4-oxo-1,8-naphthyridine-3-carboxylic acid, ethyl 7-chloro-1-cyclopropyl-6-fluoro-1,4-dihydro-4-oxo-1,8-naphthyridine-3-carboxylate, ethyl 1-cyclopropyl-6,7,8-trifluoro-1,4-dihydro-4-oxo-3-quinolinecarboxylate, 9,10-difluoro-2,3-dihydro-3-methyl-7-oxo-7H-pyrido-[1,2,3-de][1,4]benzoxacine-6-carboxylic acid, 8,9-difluoro-6,7-dihydro-5-methyl-1-oxo-1H,5H-benzo[i,j]-quinolicine-2-carboxylic acid, 7-chloro-6-fluoro-1-phenyl-1,4-dihydro-4-oxo-1,8-naphthyridine-3-carboxylic acid, ethyl 7-chloro-6-fluoro-1-(4-fluorophenyl)-1,4-dihydro-4-oxo-1,8-naphthyridine-3-carboxylate, 6,7,8-trifluoro-1,4-dihydro-1-methyl-amino-4-oxo-3-quinolinecarboxylic acid, 1-amino-6,7,8-trifluoro-1,4-dihydro-4-oxo-3-quinolinecarboxylic acid, 6,7,8-trifluoro-1,4-dihydro-1-dimethylamino-4-oxo-3-quinolinecarboxylic acid, 6,7-difluoro-1-(4-fluorophenyl)-1,4-dihydro-8-methyl-4-oxo-3-quinolinecarboxylic acid, 7-chloro-6-fluoro-1-(4-fluorophenyl)-1,4-dihydro-4-oxo-3-quinolinecarboxylic acid, 7-chloro-6-fluoro-1-(2,4-difluorophenyl)-1,4-dihydro-4-oxo-3-quinolinecarboxylic acid, 6,7,8-trifluoro-1-(4-fluorophenyl)-1,4-dihydro-4-oxo-3-quinolinecarboxylic acid, 1-cyclopropyl-6,7-difluoro-1,4-dihydro-5-methyl-4-oxo-3-quinolinecarboxylic acid, 7-chloro-1-cyclopropyl-6-fluoro-1,4-dihydro-5-methyl-4-oxo-1,8-naphthyridine-3-carboxylic acid, 7-chloro-6-fluoro-1-(2,4-difluorophenyl)-1,4-dihydro-5-methyl-4-oxo-1,8-naphthyridine-3-carboxylic acid, 6,7-difluoro-1,4-dihydro-1-(3-oxetanyl)-4-oxo-3-quinolinecarboxylic acid, 6,7,8-trifluoro-1,4-dihydro-1-(3-oxetanyl)-4-oxo-3-quinolinecarboxylic acid, 1-(bicyclo[1.1.1]pent-1-yl)-6,7,8-trifluoro-1,4-dihydro-4-oxo-3-quinolinecarboxylic acid, 7-chloro-1-(1,1-dimethylpropargyl)-6-fluoro-1,4-dihydro-4-oxo-1,8-naphthyridine-3-carboxylic acid, 6,7,8-trifluoro-1-(2,4-difluorophenyl)-1,4-dihydro-4-oxo-3-quinolinecarboxylic acid, 6,7,8-trifluoro-1,4-dihydro-4-oxo-1-phenyl-3-quinolinecarboxylic acid, 7-chloro-1-ethyl-6-fluoro-1,4-dihydro-4-oxo-1,8-naphthyridine-3-carboxylic acid, 6,7-difluoro-1,4-dihydro-4-oxo-1-vinyl-3-quinolinecarboxylic acid, 1-cyclopropyl-5,6,7,8-tetrafluoro-1,4-dihydro-4-oxo-3-quinolinecarboxylic acid, 5-amino-1-cyclopropyl-6,7,8-trifluoro-1,4-dihydro-4-oxo-3-quinolinecarboxylic acid, 1-cyclopropyl-6,7,8-trifluoro-1,4-dihydro-5-hydroxy-4-oxo-3-quinolinecarboxylic acid, 1-cyclopropyl-6,7-difluoro-1,4-dihydro-8-methoxy-4-oxo-3-quinolinecarboxylic acid, ethyl 7-chloro-1-(2,4-difluorophenyl)-6-fluoro-1,4-dihydro-4-oxo-1,8-naphthyridine-3-carboxylate, 1-cyclopropyl-6,7-difluoro-1,4-dihydro-4-oxo-8-vinyl-3-quinolinecarboxylic acid, 1-cyclopropyl-8-ethinyl-6,7-difluoro-1,4-dihydro-4-oxo-3-quinolinecarboxylic acid, 9,10-difluoro-3-methyl-7-oxo-2,3-dihydro-7H-pyrido[1,2,3-d,e][1,3,4]benzoxadiazine-6-carboxylic acid, 8-amino-9,10-difluoro-3-methyl-7-oxo-2,3-dihydro-7H-pyrido[1,2,3-d,e][1,3,4]benzoxadiazine-6-carbonyloc acid, 7,8-difluoro-5-oxo-9,1-[(N-methylimino)methanol]-5H-thiazolo[3,2-a]-quinoline-4-carboxylic acid, 7,8-difluoro-5-oxo-9,1-[(N-ethylimino)methano]-5H-thiazolo[3,2-a]-quinoline-4-carboxylic acid, 7,8-difluoro-5-oxo-9,1-(epoxymethano)-5H-thiazolo[3,4-a]-quinoline-4-carboxylic acid, 7,8-difluoro-5-oxo-9,1-(epithiomethano)-5H-thiazolo[3,2-a]-quinoline-4-carboxylic acid, 7,8-difluoro-1-methyl-5-oxo-5H-thiazolo[3,2-a]-quinoline-4-carboxylic acid, 8-bromo-6,7-difluoro-1-(cis-2-fluorocyclopropyl)-1,4-dihydro-4-oxo-3-quinolinecarboxylic acid, 8-chloro-6,7-difluoro-1-(cis-2-fluorocyclopropyl)-1,4-dihydro-4-oxo-3-quinolinecarboxylic acid, 6,7-difluoro-1-(cis-2-fluorocyclopropyl)-1,4-dihydro-4-oxo-3-quinolinecarboxylic acid, 6,7,8-trifluoro-1-(cis-2-fluorocyclopropyl)-1,4-dihydro-4-oxo-3-quinolinecarboxylic acid, 5,6,7,8-tetrafluoro-1-(cis-2-fluorocyclopropyl)-1,4-dihydro-4-oxo-3-quinolinecarboxylic acid, 6,7-difluoro-1-(cis-2-fluorocyclopropyl)-1,4-dihydro-8-methyl-4-oxo-3-quinolinecarboxylic acid, 8-ethinyl-6,7-difluoro-1-(cis-2-fluorocyclopropyl)-1,4-dihydro-4-oxo-3-quinolinecarboxylic acid, 6,7-difluoro-1-(cis-2-fluorocyclopropyl)-1,4-dihydro-4-oxo-8-trifluoromethyl-3-quinolinecarboxylic acid, 6,7-difluoro-1-(cis-2-fluorocyclopropyl)-8-difluoromethoxy-1,4-dihydro-4-oxo-3-quinolinecarboxylic acid, 6,7-difluoro-1-(cis-2-fluorocyclopropyl)-1,4-dihydro-8-methoxy-4-oxo-3-quinolinecarboxylic acid, 6,7-difluoro-1-(cis-2-fluorocyclopropyl)-1,4-dihydro-5-methyl-4-oxo-3-quinolinecarboxylic acid, 5-amino-6,7,8-trifluoro-1-(cis-2-fluorocyclopropyl)-1,4-dihydro-4-oxo-3-quinolinecarboxylic acid, 8-bromo-6,7-difluoro-1-[(1R,2S)-2-fluorocyclopropyl]-1,4-dihydro-4-oxo-3-quinolinecarboxylic acid, 8-chloro-6,7-difluoro-1-[(1R,2S)-2-fluorocyclopropyl]-1,4-dihydro-4-oxo-3-quinolinecarboxylic acid, 6,7-difluoro-1-[(1R,2S)-2-fluorocyclopropyl]-1,4-dihydro-4-oxo-3-quinolinecarboxylic acid, 6,7,8-trifluoro-1-[(1R,2S)-2-fluorocyclopropyl]-1,4-dihydro-4-oxo-3-quinolinecarboxylic acid, 5,6,7,8-tetrafluoro-1-[(1R,2S)-2-fluorocyclopropyl]-1,4-dihydro-4-oxo-3-quinolinecarboxylic acid, 6,7-difluoro-1-[(1R,2S)-2- fluorocyclopropyl]-1,4-dihydro-8-methyl-4-oxo-3-quinolinecarboxylic acid, 8-ethinyl-6,7-difluoro-1-[(1R,2S)-2-fluorocyclopropyl]-1,4-dihydro-4-oxo-3-quinolinecarboxylic acid, 6,7-difluoro-1-[(1R,2S)-2-fluorocyclopropyl]-1,4-dihydro-4-oxo-8-trifluoromethyl-3-quinolinecarboxylic acid, 6,7-difluoro-1-[(1R,2S)-2-fluorocyclopropyl]-8-difluoromethoxy-1,4-dihydro-4-oxo-3-quinolinecarboxylic acid, 6,7-difluoro-1-[(1R,2S)-2-fluorocyclopropyl]-1,4-dihydro-8-methoxy-4-oxo-3-quinolinecarboxylic acid, 6,7-difluoro-1-[(1R2S)-2-fluorocyclopropyl]-1,4-dihydro-5-methyl-4-oxo-3-quinolinecarboxylic acid and 5-amino-6,7,8-trifluoro-1-[(1R,2S)-2-fluorocyclopropyl]-1,4-dihydro-4-oxo-3-quinolinecarboxylic acid.

The tricyclic amines of the formula (III) required as starting compounds are new. They can be prepared by the methods represented in equation 1: a cyclic diene (1) is reacted with an imide (2) in the context of the Diels-Alder reaction to give the adduct (3). The compounds (3) can be broken down as nitriles (G=CH) or esters (G=COOC$_2$H$_5$) via amide intermediate stages (4) to give amines (5), which can be hydrogenated, for example with complex hydrides, to give the tricyclic diamines (6). If the radical R in (6) represents benzyl, this can be split off by hydrogenolysis with simultaneous hydrogenation of the double bond to form the saturated tricyclic diamine (7). The compounds (3) with substituents such as, for example, G=OCH$_3$, OH, CN, COOC$_2$H$_5$ or N(CH$_3$)$_2$ can also be reduced directly with complex hydrides to give the compounds (8), and these can then be hydrogenated to give the saturated tricyclic diamines (9). Selectively acylated diamines can be prepared, for example via tertbutoxycarbonylation of the compound (6) (R=benzyl) and subsequent hydrogenation to give (10). Monomethylated diamines (11) or (12) can be prepared, for example, via acylation of (5) with a chloroformic acid ester and subsequent reduction to give (11) or (12). The compounds (6) to (12) shown in the equation correspond to the general structure (III) if R denotes H.

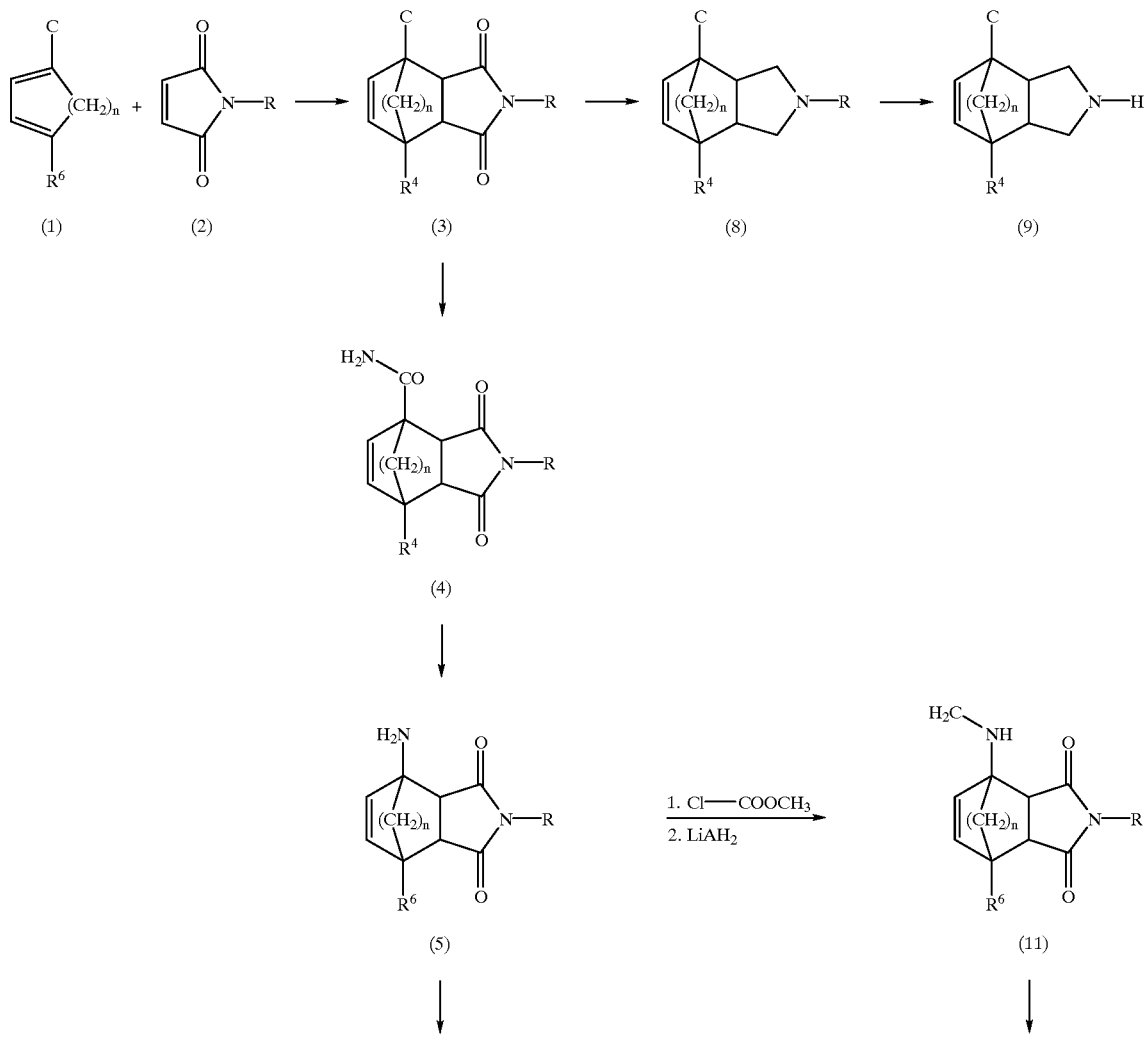

Equation 1

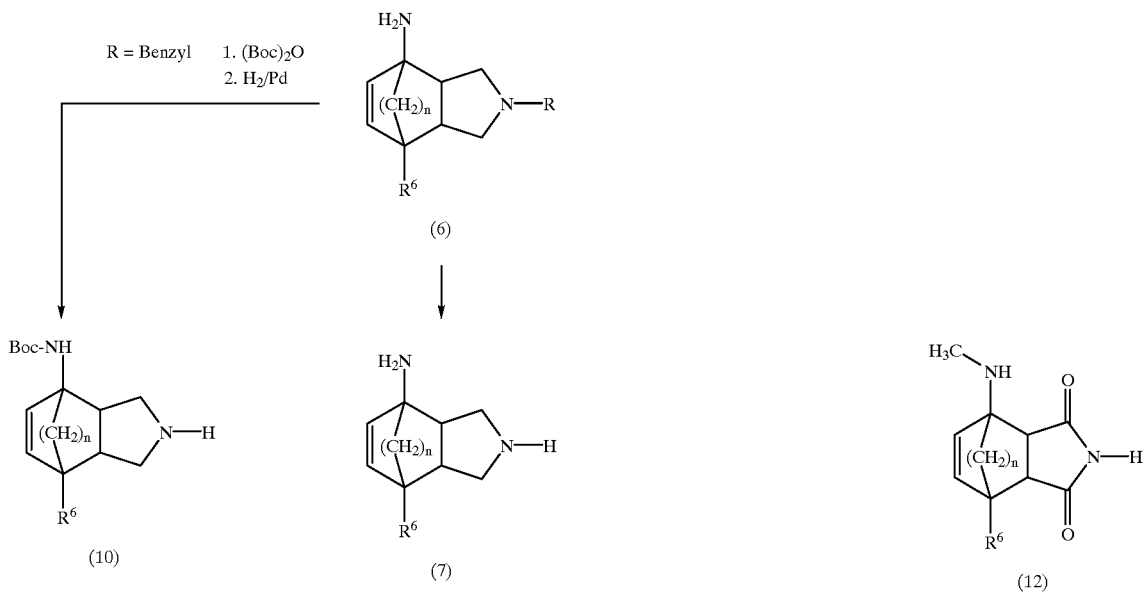

G = for example OCH₃, O——COCH₃, CN, COOC₂H₅, N(CH₃)₂
G' = for example OCH₃, OH, CH₂NH₂, CH₂OH, N(CH₃)₂
R = H, tert-butyl, Si(CH₃)₃, benzyl, α-methylbenzyl
n and R⁶ = as stated above Examples which may be mentioned of tricyclic amines of the formula (III) are:

4-azatricyclo[5.2.1.0$^{2,6}$]dec-8-en-1-ylamine, 4-azatricyclo[5.2.2.0$^{2,6}$]undec-8-en-1-ylamine, 4-azatricyclo[5.2.1.0$^{2,6}$]dec-8-en-1-ylamine-N-carboxylic acid tert-butyl ester, 4-azatricyclo[5.2.2.0$^{2,6}$]undec-8-en-1-ylamine-N-carboxylic acid tert-butyl ester, (4-azatricyclo[5.2.1.0$^{2,6}$]dec-8-en-1-yl)-methyl-amine, (4-azatricyclo[5.2.2.0$^{2,6}$]undec-8-en-1-yl)-methyl-amine, (4-azatricyclo[5.2.1.0$^{2,6}$]dec-8-en-1-yl)-dimethyl-amine, (4-azatricyclo[5.2.2.0$^{2,6}$]undec-8-en-1yl)-dimethyl-amine, 7-methyl-4-azatricyclo[5.2.1.0$^{2,6}$]dec-8-en-1-yl-amine, 7-methyl-4-azatricyclo[5.2.2.0$^{2,6}$]undec-8-en-1yl-amine, methyl-(7-methyl-4-azatricyclo[5.2.1.0$^{2,6}$]dec-8-en-1-yl)-amine, methyl-(7-methyl-4-azatricyclo[5.2.2.0$^{2,6}$]undec-8-en-1-yl)amine, dimethyl-(7-methyl-4-azatricyclo[5.2.1.0$^{2,6}$]dec-8-en-1-yl)-amine, dimethyl-(7-methyl-4-azatricyclo[5.2.2.0$^{2,6}$]undec-8-en-1-yl)-amine, (4-azatricyclo[5.2.1.0$^{2,6}$]dec-8-en-1-yl-methyl)-amine, (4-azatricyclo[5.2.2.0$^{2,6}$]undec-8-en-1-ylmethyl)amine,4-azatricyclo-[5.2.1.0$^{2,6}$]dec-8-en-1-ol, 4-azatricyclo[5.2.2.0$^{2,6}$]undec-8-en-1-ol, (4-azatricyclo-[5.2.1.0$^{2,6}$]dec-8-en-1-yl)-methanol, (4-azatricyclo[5.2.2.0$^{2,6}$]undec-8-en-1-yl)-methanol, 4-azatricyclo[5.2.1.0$^{2,6}$]dec-1-ylamine, 4-azatricyclo[5.2.2.0$^{2,6}$]undec-1-ylamine, tert-butyl 4-azatricyclo[5.2.1.0$^{2,6}$]dec-1-ylamine-N-carboxylate, tert-butyl 4-azatricyclo[5.2.2.0$^{2,6}$]undec-1-ylamine-N-carboxylate, (4-azatricyclo[5.2.1.0$^{2,6}$]dec-1-yl)-methyl-amine, (4-azatricyclo[5.2.2.0$^{2,6}$]undec-1-yl)-methyl-amine, (4-azatricyclo[5.2.1.0$^{2,6}$]dec-1-yl)-dimethyl-amine, (4-azatricyclo[5.2.2.0$^{2,6}$]undec-1-yl)-dimethyl-amine, 7-methyl-4-azatricyclo[5.2.1.0$^{2,6}$]dec-1-yl-amine, 7-methyl-4-azatricyclo[5.2.2.0$^{2,6}$]undec-1-amine, methyl-(7-methyl-4-azatricyclo[5.2.1.0$^{2,6}$]dec-1-yl)-amine, methyl-(7-methyl-4-azatricyclo[5.2.2.0$^{2,6}$]undec-1-yl)-amine, dimethyl-(7-methyl-4-azatricyclo[5.2.1.0$^{2,6}$]dec-1-yl)-amine, dimethyl-(7-methyl-4-azatricyclo[5.2.2.0$^{2,6}$]undec-1-yl)-amine, (4-azatricyclo[5.2.1.0$^{2,6}$]dec-1-ylmethyl) amine, (4-azatricyclo[5.2.2.0$^{2,6}$]undec-1-methyl)amine, 4-azatricyclo[5.2.1.0$^{2,6}$]dec-1-ol, 4-azatricyclo[5.2.2.0$^{2,6}$]undec-1-ol, (4-azatricyclo[5.2.1.0$^{2,6}$]dec-1-yl)-methanol and (4-azatricyclo[5.2.2.0$^{2,6}$]undec-1-yl)-methanol.

The enantiomerically pure compounds of the formula (III) used as starting compounds can be prepared by the following process:

1. The racemic tricyclic amines (III) can be reacted with enantiomerically pure acids, for example carboxylic acids or sulphonic acids, such as N-acetyl-L-glutamic acid, N-benozyl-L-alanine, 3-bromo-camphor-9-sulphonic acid, camphor-3-carboxylic acid, cis-camphor acid, camphor-10-sulphonic acid, O,O'-dibenzoyl-tartaric acid, D- or L-tartaric acid, mandelic acid, α-methoxy-phenylacetic acid, 1-phenyl-ethanesulphonic acid or α-phenyl-succinic acid, to give a mixture of the diastereomeric salts, which can be separated into the diastereomerically pure salts by fractional crystallization (see P. Newman, Optical Resolution Procedures for Chemical Compounds, Volume 1). The enantiomerically pure amines can be liberated by treatment of these salts with alkali metal hydroxides or alkaline earth metal hydroxides.

2. In a manner similar to that described under 1., splitting of racemates of the basic intermediate stages which occur during preparation of the racemic dicyclic amines can be carried out with the abovementioned enantiomerically pure acids. Examples of such basic intermediate stages are compounds having the structure (5) in equation 1.

3. Both the racemic amines (III) and the intermediate stages in their preparation, such as, for example, compounds having the structures (3) to (5) in equation 1, can be separated by chromatography over chiral carrier materials, if appropriate after acylation (see, for example, G. Blaschke, Angew. Chem. 92, 14 [1980]).

4. Both the racemic amines (III) and basic intermediate stages, such as, for example, compounds having the structure (5) in equation 1, can be converted by chemical linking to chiral acyl radicals into diastereomer mixtures, which can be separated by distillation, crystallization or chromatography into the diastereomerically pure acyl derivatives, from which the enantiomerically pure amines can be isolated by hydrolysis. Examples of reagents for linking with chiral acyl radicals are: α-methoxy-α-trifluoromethyl-phenylacetyl chloride, menthyl isocyanate, D- or L-α-phenyl-ethyl isocyanate, menthyl chloroformate and camphor-10-sulphonyl chloride.

5. In the course of the synthesis of the tricyclic amines (III), chiral protective groups can also be introduced instead of achiral protective groups. Diastereomers which can be separated are obtained in this manner. For example, in the synthesis of the compound (3) in equation 1, the benzyl radical can be replaced by the α-phenylethyl radical having the R or S configuration.

The reaction of (II) with (III), in which the compounds (III) can also be employed in the form of their salts, such as, for example, the hydrochlorides, is preferably carried out in a diluent, such as dimethyl sulphoxide, N,N-dimethylformamide, N-methylpyrrolidone, hexamethyl-phosphoric acid trisamide, sulpholane, acetonitrile, water, an alcohol, such as methanol, ethanol, n-propanol, isopropanol or glycol monomethyl ether, or pyridine. Mixtures of these diluents can also be used.

Acid-binding agents which can be used are all the customary inorganic and organic acid-binding agents. These include, preferably, the alkali metal hydroxides, alkali metal carbonates, organic amines and amidines. Specific agents which may be mentioned as particularly suitable are: triethylamine, 1,4-diazabicyclo[2.2.2]octane (DABCO), 1,8-diazabicyclo[5.4.0]undec-7-ene (DBU) or excess amine (III).

The reaction temperatures can be varied within a relatively wide range. In general, the reaction is carried out at between about 20 and 200° C., preferably between 80 and 160° C.

The reaction can be carried out under normal pressure, but also under increased pressure. In general, it is carried out under pressures of between about 1 and 100 bar, preferably between 1 and 10 bar.

In carrying out the process according to the invention, 1 to 15 mol, preferably 1 to 5 mol, of the compound (III) are employed per mole of compound (II).

Free amino groups can be protected by a suitable amino protective group, such as, for example, by the tert-butoxycarbonyl radical or an azomethine protective group, during the reaction and liberated again when the reaction has ended.

To prepare the ester according to the invention, the underlying carboxylic acid is preferably reacted in excess alcohol in the presence of strong acids, such as sulphuric acid, anhydrous hydrogen chloride, methanesulphonic acid, p-toluenesulphonic acid or acid ion exchangers, at temperatures of about 20 to 180° C., preferably about 60 to 120° C. The water of reaction formed can also be removed by azeotropic distillation with chloroform, carbon tetrachloride or toluene.

The esters can also advantageously be prepared by heating the underlying acid with dimethylformamide dialkyl acetal in a solvent, such as dimethylformamide.

The esters used as prodrugs, such as, for example, the (5-methyl-2-oxo-1,3-dioxol-4-ylmethyl) ester, are obtained by reacting an alkali metal salt of the underlying carboxylic acid, which can optionally be protected by a protective group on the N atom, with 4-bromomethyl- or 4-chloromethyl-5-methyl-1,3-dioxol-2-one in a solvent, such as dimethylformamide, dimethylacetamide, N-methyl-pyrrolidone, dimethyl sulphoxide or tetramethylurea, at temperatures of about 0 to 100° C., preferably 0 to 50° C.

The acid addition salts of the compounds according to the invention are prepared in the customary manner, for example by dissolving in excess aqueous acid and precipitating the salt with a water-miscible solvent, such as methanol, ethanol, acetone or acetonitrile. It is also possible to heat an equivalent amount of betaine and acid in water or an alcohol, such as glycol monomethyl ether, and then to evaporate the mixture to dryness or to filter off the precipitated salt with suction. Pharmaceutically usable salts are to be understood as meaning, for example, the salts of hydrochloric acid, sulphuric acid, acetic acid, glycolic acid, lactic acid, succinic acid, citric acid, tartaric acid, 2-hydroxyglutaric acid, methanesulphonic acid, 4-toluenesulphonic acid, galacturonic acid, glucuronic acid, 5-oxotetrahydrofuran-2-carboxylic acid, embonic acid, glutamic acid or aspartic acid.

The alkali metal and alkaline earth metal salts of the carboxylic acids according to the invention are obtained, for example, by dissolving the betaine in excess alkali metal hydroxide solution or alkaline earth metal hydroxide solution, filtration to remove the undissolved betaine and evaporation of the filtrate to dryness. The sodium, potassium and calcium salts are pharmaceutically suitable. The corresponding silver salts are obtained by reaction of an alkali metal salt or alkaline earth metal salt with a suitable silver salt, such as silver nitrate.

In addition to the active compounds mentioned in the examples, the active compounds mentioned below and those listed in Tables 1 to 8 can also be prepared, and can exist either as racemates or as enantiomerically pure compounds, or else where appropriate as diastereomer mixtures or as diastereomerically pure compounds:

8-(1-amino-4-azatricyclo[5.2.1.0$^{2,6}$]dec-8-en-4-yl)-7-fluoro-5-oxo-9,1-(epoxymethano)-5H-thiazolo[3,2-a]quinoline-4-carboxylic acid, 8-(1-methylamino-4-azatricyclo[5.2.1.0$^{2,6}$]dec-8-en-4-yl)-7-fluoro-5-oxo-9,1-(epoxymethano)-5H-thiazolo[3,2-a]quinoline-4-carboxylic acid, 8-(1-amino-7-methyl-4-azatricyclo[5.2.1.0$^{2,6}$]dec-8-en-4-yl)-7-fluoro-5-oxo-9,1-(epoxymethano)-5H-thiazolo[3,2-a]quinoline-4-carboxylic acid, 8-(1-amino-4-azatricyclo[5.2.1.0$^{2,6}$]dec-4-yl)-7-fluoro-5-oxo-9,1-(epoxymethano)-5H-thiazolo[3,2-a]quinoline-4-carboxylic acid, 8-(1-methylamino-4-azatricyclo[5.2.1.0$^{2,6}$]dec-4-yl)-7-fluoro-5-oxo-9,1-(epoxymethano)-5H-thiazolo[3,2-a]quinoline-4-carboxylic acid, 8-(1-amino-7-methyl-4-azatricyclo[5.2.1.0$^{2,6}$]dec-4-yl)-7-fluoro-5-oxo-9,1-(epoxymethano)-5H-thiazolo[3,2-a]quinoline-4-carboxylic acid, 8-(1-amino-4-azatricyclo[5.2.1.0$^{2,6}$]dec-8-en-4-yl)-7-fluoro-5-oxo-9,1-[N-methylimino)methano]-5H-thiazolo[3,2-a]quinoline-4-carboxylic acid, 8-(1-methylamino-4-azatricyclo[5.2.1.0$^{2,6}$]dec-8-en-4-yl)-7-fluoro-5-oxo-9,1-[(N-methyl-imino)methano]-5H-thiazolo[3,2-a]quinoline-4-carboxylic acid, 8-(1-amino-7-methyl-4-azatricyclo[5,2,1,0$^{2,6}$]dec-8-en-4-yl)-7-fluoro-5-oxo-9,1-[(N-methyl-imino)methano]-5H-thiazolo[3,2-a]quinoline-4-carboxylic acid, 8-(1-amino-4-azatricyclo[5.2.1.0$^{2,6}$]dec-4-yl)-7-fluoro-5-oxo-9,1-[(N-methyl-imino)methano]-5H-thiazolo[3,2-a]quinoline-4-carboxylic acid, 8-(1-methylamino-4-azatricyclo[5,2,1,0$^{2,6}$]dec-4-yl)-7-fluoro-5-oxo-9,1-[(N-methyl-imino)methano]-5H-thiazolo[3,2-a]quinoline-4-carboxylic acid, 8-(1-amino-7-methyl-4-azatricyclo[5.2.1.0$^{2,6}$]dec-4-yl)-7-fluoro-5-oxo-9,1-[(N-methyl-imino)methano]-5H-thiazolo[3,2-a]quinoline-4-carboxylic acid, 8-amino-10-(1-amino-4-azatricyclo[5.2.1.0$^{2,6}$]decan-4-yl)-9-fluoro-3-methyl-7-oxo-2,3-dihydro-7H-pyrido[1,2,3-d,e][1,3,4]benzoxadiazine-6-carboxylic acid, 10-(1-amino-4-azatricyclo-[5.2.1.0$^{2,6}$]decan-4-yl)-9-fluoro-3-methyl-7-oxo-2,3-dihydro-7H-pyrido[1,2,3-d,e]-[1,3,4] benzoxadiazine-6-carboxylic acid, 10-(1-amino-7-methyl-4-azatricyclo[5.2.1.0$^{2,6}$]decan-4-yl)-9-fluoro-3-methyl-7-oxo-2,3-dihydro-7H-pyrido[1,2,3-d,e][1,3,4]

benzoxadiazine-6-carboxylic acid, 10-(1-methylamino-4-azatricyclo[5,2,1,0²,⁶-]decan-4-yl)-9-fluoro-3-methyl-7-oxo-2,3-dihydro-7H-pyrido[1,2,3-d,e][1,3,4]-benzoxadiazine-6-carboxylic acid, 10-(1-amino-4-azatricyclo[5.2.1.0²,⁶]dec-8-en-4-yl)-9-fluoro-3-methyl-7-oxo-2,3-dihydro-7H-pyrido[1,2,3-d,e][1,3,4]benzoxadiazine-6-carboxylic acid, 10-(1-methylamino-4-azatricyclo[5.2.1.0²,⁶]dec-8-en-4-yl)-9-fluoro-3-methyl-7-oxo-2,3-dihydro-7H-pyrido[1,2,3-d,e][1,3,4]benzoxadiazine-6-carboxylic acid, 10-(1-amino-7-methyl-4-azatricyclo[5.2.1.0²,⁶]dec-8-en-4-yl)-9-fluoro-3-methyl-7-oxo-2,3-dihydro-7H-pyrido[1,2,3-d,e][1,3,4]benzoxadiazine-6-carboxylic acid, 10-(1-amino-4-azatricyclo[5.2.2.0²,⁶]undec-8-en-4-yl)-9-fluoro-3-methyl-7-oxo-2,3-dihydro-7H-pyrido[1,2,3-d,e][1,4]benzoxazine-6-carboxylic acid, 10-(1-amino-4-azatricyclo[5.2.2.0²,⁶]undecan-4-yl)-9-fluoro-3-methyl-7-oxo-2,3-dihydro-7H-pyrido[1,2,3-d,e][1,3,4]benzoxadiazine-6-carboxylic acid, 8-amino-10-(1-amino-4-azatricyclo[5.2.1.0²,⁶]decan-4-yl)-9-fluoro-3-methyl-7-oxo-2,3-dihydro-7H-pyrido[1,2,3-d,e][1,4]benzoxazine-6-carboxylic acid, 10-(1-amino-4-azatricyclo[5.2.1.0²,⁶]decan-4-yl)-9-fluoro-3-methyl-7-oxo-2,3-dihydro-7H-pyrido[1,2,3-d,e][1,4]benzoxazine-6-carboxylic acid, 10-(1-amino-7-methyl-4-azatricyclo[5.2.1.0²,⁶]decan-4-yl)-9-fluoro-3-methyl-7-oxo-2,3-dihydro-7H-pyrido[1,2,3-d,e][1,4]benzoxazine-6-carboxylic acid, 10-(1-methylamino-4-azatricyclo[5.2.1.0²,⁶]decan-4-yl)-9-fluoro-3-methyl-7-oxo-2,3-dihydro-7H-pyrido[1,2,3-d,e][1,3,4]benzoxadiazine-6-carboxylic acid, 10-(1-amino-4-azatricyclo[5.2.1.0²,⁶]dec-8-en-4-yl)-9-fluoro-3-methyl-7-oxo-2,3-dihydro-7H-pyrido[1,2,3-d,e][1,4]benzoxazine-6-carboxylic acid, 10-(1-methylamino-4-azatricyclo[5.2.1.0²,⁶]dec-8-en-4-yl)-9-fluoro-3-methyl-7-oxo-2,3-dihydro-7H-pyrido[1,2,3-d,e][1,4]benzoxazine-6-carboxylic acid, 10-(1-amino-7-methyl-4-azatricyclo[5.2.1.0²,⁶]dec-8-en-4-yl)-9-fluoro-3-methyl-7-oxo-2,3-dihydro-7H-pyrido[1,2,3-d,e][1,4]benzoxazine-6-carboxylic acid, 8-(1-aminomethyl-4-azatricyclo[5.2.1.0²,⁶]dec-4-yl)-7-fluoro-5-oxo-9,1-(epoxymethano)-5H-thiazolo[3,2-a]quinoline-4-carboxylic acid, 8-(1-aminomethyl-4-azatricyclo[5.2.2.0²,⁶]undec-4-yl)-7-fluoro-5-oxo-9,1-(epoxymethano)-5H-thiazolo[3,2-a]quinoline-4-carboxylic acid, 8-(1-aminomethyl-4-azatricyclo[5.2.1.0²,⁶]dec-8-en-4-yl)-7-fluoro-5-oxo-9,1-(epoxymethano)-5H-thiazolo[3,2-a]quinoline-4-carboxylic acid, 8-(1-aminomethyl-4-azatricyclo[5.2.2.0²,⁶]undec-8-en-4-yl)-7-fluoro-5-oxo-9,1-(epoxymethano)-5H-thiazolo[3,2-a]quinoline-4-carboxylic acid, 8-(1-aminomethyl-4-azatricyclo[5.2.1.0²,⁶]dec-4-yl)-7-fluoro-5-oxo-9,1-[(N-methyl-imino)methano]-5H-thiazolo[3,2-a]quinoline-4-carboxylic acid, 8-(1-aminomethyl-4-azatricyclo[5.2.2.0²,⁶]undec-4yl)-7-fluoro-5-oxo-9,1[(N-methyl-imino)methano]-5H-thiazolo[3,2-a]quinoline-4-carboxylic acid, 8-(1-aminomethyl-4-azatricyclo-[5.2.1.0²,⁶]dec-8-en-4-yl)-7-fluoro-5-oxo-9,1-[(N-methyl-imino)methano]-5H-thiazolo[3,2-a]quinoline-4-carboxylic acid, 8-(1-aminomethyl-4-azatricyclo-[5.2.2.0²,⁶]undec-8-en-4-yl)-7-fluoro-5-oxo-9,1[(N-methyl-imino)methano]-5H-thiazolo[3,2-a]quinoline-4-carboxylic acid, 10-(1-aminomethyl-4-azatricyclo-[5.2.1.0²,⁶]dec-4-yl)-9-fluoro-3-methyl-7-oxo-2,3-dihydro-7H-pyrido[1,2,3-d,e][1,3,4]benzoxadiazine-6-carboxylic acid, 10-(1-aminomethyl-4-azatricyclo[5.2.2.0²,⁶]-undec-4-yl)-9-fluoro-3-methyl-7-oxo-2,3-dihydro-7H-pyrido[1,2,3-d,e][1,3,4]-benzoxadiazine-6-carboxylic acid, 10-(1-aminomethyl-4-azatricyclo[5.2.1.0²,⁶]dec-8en-4-yl)-9-fluoro-3-methyl-7-oxo-2,3-dihydro-7H-pyrido[1,2,3-d,e][1,3,4]benzoxadiazine-6-carboxylic acid and 10-(1-aminomethyl-4-azatricyclo[5.2.2.0²,⁶]undec-8-en-4-yl)-9-fluoro-3-methyl-7-oxo-2,3-dihydro-7H-pyrido[1,2,3-d,e][1,3,4]benzoxadiazine-6-carboxylic acid.

TABLE 1

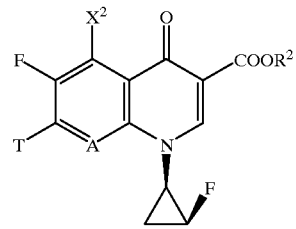

| T* | A | $X^2$ | $R^2$ |
|---|---|---|---|
| $T^I$ | C—H | H | H |
| $T^I$ | C—F | H | H |
| $T^I$ | C—Cl | H | H |
| $T^I$ | C—$CH_3$ | H | H |
| $T^I$ | C—$OCH_3$ | H | H |
| $T^I$ | N | H | H |
| $T^I$ | C—F | F | H |
| $T^I$ | C—F | $NH_2$ | H |
| $T^I$ | C—F | H | $C_2H_5$ |
| $T^I$ | C—Cl | H | $C_2H_5$ |
| $T^{II}$ | C—H | H | H |
| $T^{II}$ | C—F | H | H |
| $T^{II}$ | C—Cl | H | H |
| $T^{II}$ | C—$CH_3$ | H | H |
| $T^{II}$ | C—$OCH_3$ | H | H |
| $T^{II}$ | N | H | H |
| $T^{II}$ | C—F | F | H |

*$T^I$ = 1-Amino-4-aza-tricyclo[5.2.1.0²,⁶]dec-8-en-4-yl
$T^{II}$ = 7-Methyl-1-amino-4-aza-tricyclo[5.2.1.0²,⁶]dec-8-en-4-yl

TABLE 2

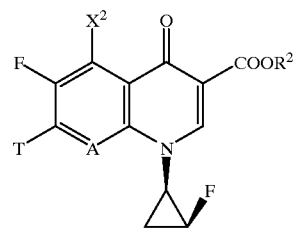

| T* | A | $X^2$ | $R^2$ |
|---|---|---|---|
| $T^{III}$ | C—H | H | H |
| $T^{III}$ | C—F | H | H |
| $T^{III}$ | C—Cl | H | H |
| $T^{III}$ | C—$CH_3$ | H | H |
| $T^{III}$ | C—$OCH_3$ | H | H |
| $T^{III}$ | N | H | H |
| $T^{III}$ | C—F | F | H |
| $T^{III}$ | C—F | $NH_2$ | H |
| $T^{III}$ | C—F | H | $C_2H_5$ |
| $T^{III}$ | C—Cl | H | $C_2H_5$ |
| $T^{IV}$ | C—H | H | H |
| $T^{IV}$ | C—F | H | H |
| $T^{IV}$ | C—Cl | H | H |
| $T^{IV}$ | C—$CH_3$ | H | H |
| $T^{IV}$ | C—$OCH_3$ | H | H |
| $T^{IV}$ | N | H | H |
| $T^{IV}$ | C—F | F | H |

*$T^{III}$ = 1-Methylamino-4-aza-tricyclo[5.2.1.0²,⁶]dec-8-en-4-yl
$T^{IV}$ = 1-Aminomethyl-4-aza-tricyclo[5.2.1.0²,⁶]dec-8-en-4-yl

TABLE 3

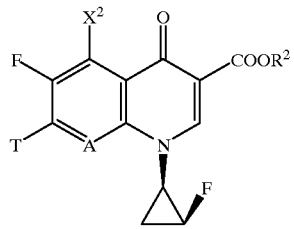

| T* | A | X² | R² |
|---|---|---|---|
| T^V | C—H | H | H |
| T^V | C—F | H | H |
| T^V | C—Cl | H | H |
| T^V | C—CH₃ | H | H |
| T^V | C—OCH₃ | H | H |
| T^V | N | H | H |
| T^V | C—F | F | H |
| T^V | C—F | NH₂ | H |
| T^V | C—F | H | C₂H₅ |
| T^V | C—Cl | H | C₂H₅ |
| T^VI | C—H | H | H |
| T^VI | C—F | H | H |
| T^VI | C—Cl | H | H |
| T^VI | C—CH₃ | H | H |
| T^VI | C—OCH₃ | H | H |
| T^VI | N | H | H |
| T^VI | C—F | F | H |

*T^V = 1-Amino-4-aza-tricyclo[5.2.2.0$^{2,6}$]undec-8-en-4-yl
T^VI = 1-Amino-4-aza-tricyclo[5.2.1.0$^{2,6}$]dec-4-yl

TABLE 4

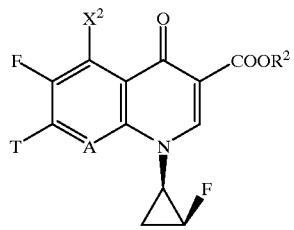

| T* | A | X² | R² |
|---|---|---|---|
| T^VII | C—H | H | H |
| T^VII | C—F | H | H |
| T^VII | C—Cl | H | H |
| T^VII | C—CH₃ | H | H |
| T^VII | C—OCH₃ | H | H |
| T^VII | N | H | H |
| T^VII | C—F | F | H |
| T^VII | C—F | NH₂ | H |
| T^VII | C—F | H | C₂H₅ |
| T^VII | C—Cl | H | C₂H₅ |
| T^VIII | C—H | H | H |
| T^VIII | C—F | H | H |
| T^VIII | C—Cl | H | H |
| T^VIII | C—CH₃ | H | H |
| T^VIII | C—OCH₃ | H | H |
| T^VIII | N | H | H |
| T^VIII | C—F | F | H |

*T^VII = 1-Amino-4-aza-tricyclo[5.2.2.0$^{2,6}$]undec-4-yl
T^VIII = 1-Methylamino-4-aza-tricyclo[5.2.1.0$^{2,6}$]dec-4-yl

TABLE 5

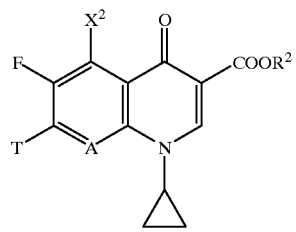

| T* | A | X² | R² |
|---|---|---|---|
| T^I | C—H | H | H |
| T^I | C—F | H | H |
| T^I | C—Cl | H | H |
| T^I | C—CH₃ | H | H |
| T^I | C—OCH₃ | H | H |
| T^I | N | H | H |
| T^I | C—F | F | H |
| T^I | C—F | NH₂ | H |
| T^I | C—F | H | C₂H₅ |
| T^I | C—Cl | H | C₂H₅ |
| T^I | C—C≡CH | H | H |
| T^I | C—CH=CH₂ | H | H |
| T^I | C—OCHF₂ | H | H |
| T^V | C—CH₃ | H | H |
| T^V | C—F | F | H |
| T^V | C—F | NH₂ | H |
| T^V | N | H | H |

*T^V = 1-Amino-4-aza-tricyclo[5.2.1.0$^{2,6}$]undec-8-en-4-yl
T^VI = 1-Amino-4-aza-tricyclo[5.2.2.0$^{2,6}$]dec-4-yl

TABLE 6

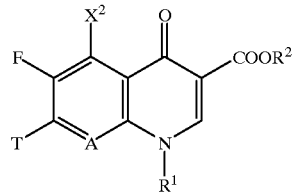

| T* | A | X² | R¹ | R² |
|---|---|---|---|---|
| T^I | C—H | H | C(CH₃)₃ | H |
| T^V | N | H | C(CH₃)₃ | H |
| T^I | N | H | C(CH₃)₃ | H |
| T^V | N | CH₃ | C(CH₃)₃ | H |
| T^V | C—F | H | C(CH₃)₃ | H |
| T^I | C—H | H | Fluoro-tert-butyl | H |
| T^V | C—H | H | Fluoro-tert-butyl | H |
| T^I | N | H | Fluoro-tert-butyl | H |
| T^V | N | H | Fluoro-tert-butyl | H |
| T^V | C—OCH₃ | H | Fluoro-tert-butyl | H |
| T^I | C—H | H | 2,4-Difluorophenyl | H |
| T^V | C—H | H | 2,4-Difluorophenyl | H |
| T^I | C—F | H | 2,4-Difluorophenyl | H |
| T^V | C—F | H | 2,4-Difluorophenyl | H |
| T^I | N | H | 2,4-Difluorophenyl | H |
| T^V | N | H | 2,4-Difluorophenyl | H |
| T^V | N | H | 2,4-Difluorophenyl | C₂H₅ |

*T^I = 1-Amino-4-aza-tricyclo[5.2.1.0$^{2,6}$]dec-8-en-4-yl
T^V = 1-Amino-4-aza-tricyclo[5.2.2.0$^{2,6}$]undec-8-en-4-yl

TABLE 7

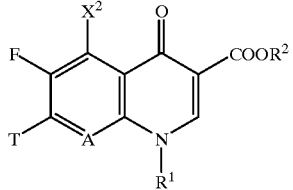

| T* | A | X² | R¹ | R² |
|---|---|---|---|---|
| T^I | C—H | H | Bicyclo[1.1.1]pent-1-yl | H |
| T^V | C—H | H | Bicyclo[1.1.1]pent-1-yl | H |
| T^I | N | H | Bicyclo[1.1.1]pent-1-yl | H |
| T^V | N | CH₃ | Bicyclo[1.1.1]pent-1-yl | H |
| T^I | C—F | H | Bicyclo[1.1.1]pent-1-yl | H |
| T^V | C—F | H | Bicyclo[1.1.1]pent-1-yl | H |
| T^I | C—OCH₃ | H | Bicyclo[1.1.1]pent-1-yl | H |
| T^V | C—OCH₃ | H | Bicyclo[1.1.1]pent-1-yl | H |
| T^I | C—H | H | 3-Oxetanyl | H |
| T^V | C—H | H | 3-Oxetanyl | H |
| T^I | N | H | 3-Oxetanyl | H |
| T^V | N | H | 3-Oxetanyl | H |
| T^I | C—F | H | 3-Oxetanyl | H |
| T^V | C—F | H | 3-Oxetanyl | H |
| T^I | C—OCH₃ | H | 3-Oxetanyl | H |
| T^V | C—OCH₃ | H | 3-Oxetanyl | H |
| T^V | C—H | H | 4-Fluorophenyl | C₂H₅ |

*T^I = 1-Amino-4-aza-tricyclo[5.2.1.0$^{2,6}$]dec-8-en-4-yl
T^V = 1-Amino-4-aza-tricyclo[5.2.2.0$^{2,6}$]undec-8-en-4-yl

TABLE 8

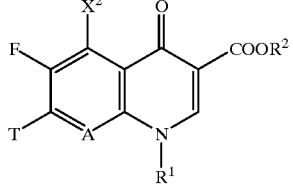

| T* | A | X² | R¹ | R² |
|---|---|---|---|---|
| T^I | C—OCH₃ | H | CH₂CH₂F | H |
| T^V | C—OCH₃ | H | CH₂CH₂F | H |
| T^I | C—OCH₃ | H | CH=CH₂ | H |
| T^V | C—OCH₃ | H | CH=CH₂ | H |
| T^I | C—OCH₃ | H | 4-Fluorophenyl | H |
| T^V | C—OCH₃ | H | 4-Fluorophenyl | H |
| T^I | C—OCH₃ | H | Cyclopropyl | (5-Methyl-2-oxo-1,3-dioxol-4-yl)-methyl |
| T^V | C—OCH₃ | H | Cyclopropyl | (5-Methyl-2-oxo-1,3-dioxol-4-yl)-methyl |
| T^I | C—H | H | Cyclopropyl | (5-Methyl-2-oxo-1,3-dioxol-4-yl)-methyl |
| T^V | C—H | H | Cyclopropyl | (5-Methyl-2-oxo-1,3-dioxol-4-yl)-methyl |
| T^I | C—F | H | Cyclopropyl | (5-Methyl-2-oxo-1,3-dioxol-4-yl)-methyl |
| T^V | C—F | H | Cyclopropyl | (5-Methyl-2-oxo-1,3-dioxol-4-yl)-methyl |
| T^V | C—OCH₃ | H | Cyclopropyl | Acetoxymethyl |
| T^V | C—OCH₃ | H | Cyclopropyl | Pivaloyloxymethyl |
| T^V | C—OCH₃ | H | 1,1-Dimethylpropargyl | H |

TABLE 8-continued

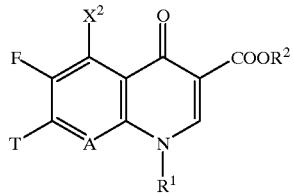

| T* | A | X² | R¹ | R² |
|---|---|---|---|---|
| T^V | C—OCH₃ | H | Methylamino | H |
| T^V | C—H | H | tert-Butyl | (5-Methyl-2-oxo-1,3-dioxol-4-yl)-methyl |

*T^I = 1-Amino-4-aza-tricyclo[5.2.1.0$^{2,6}$]dec-8-en-4-yl
T^V = 1-Amino-4-aza-tricyclo[5.2.2.0$^{2,6}$]undec-8-en-4-yl The compounds according to the invention have a potent antibiotic action and display a broad antibacterial spectrum against Gram-positive and Gram-negative germs, above all including those which are resistant to various antibiotics, such as, for example, penicillins, cephalosporins, aminoglycosides, sulphonamides, tetracyclines and against commercially available quinolines, coupled with a low toxicity.

These valuable properties enable them to be used as chemotherapeutic active compounds in medicine and as substances for the preservation of inorganic and organic materials, for example polymers, lubricants, paints, fibres, leather, paper and wood, and of foodstuffs and water.

The compounds according to the invention are active against a very broad spectrum of microorganisms. Gram-negative and Gram-positive bacteria and bacteria-like microorganisms can be combated and the diseases caused by these pathogens can be prevented, alleviated and/or cured with the aid of these compounds.

The compounds according to the invention are distinguished by an intensified action against dormant germs. The compounds have a potent bactericidal action on dormant bacteria, that is to say bacteria which show no detectable growth. This relates not only to the amount to be employed, but also to the rate of destruction. Such results have been found on Gram-positive and Gram-negative bacteria, in particular on *Staphylococcus aureus, Pseudomonas aeruginosa, Enterococcus faecalis* and *Escherichia coli*.

The compound according to the invention are particularly active against typical and atypical Mycobacteria and *Helicobacter pylori*, and also against bacteria-like microorganisms, such as, for example, Mycoplasma and Rickettsia. They are therefore particularly suitable in human and veterinary medicine for the prophylaxis and chemotherapy of local and systemic infections caused by these pathogens.

The compounds are furthermore particularly suitable for combating protozoonoses and helminthoses.

The compounds according to the invention can be used in various pharmaceutical formulations. Preferred pharmaceutical formulations which may be mentioned are tablets, coated tablets, capsules, pills, granules, suppositories, solutions, suspensions and emulsions, pastes, ointments, gels, creams, lotions, powders and sprays.

The compounds according to the invention can also be linked to β-lactam derivatives, such as, for example, cephalosporins or penems, by covalent bonds to give so-called dual action derivatives.

The following Tables 1 and 2 show the minimum inhibitory concentrations as a measure of the antibacterial activity and the $ID_{50}$ values as a measure of the genotoxic potential of a substance both for compounds according to the invention and for reference compounds from the prior art (EP 520 240).

The minimum inhibitory concentrations (MIC) were determined by a series dilution method on Iso-Sensitest agar (Oxoid). For each test substance, a series of agar plates each comprising concentrations of the active compound decreasing by double dilution in each case was prepared. The agar plates were inoculated with a multipoint inoculator (Denley). Overnight cultures of the pathogens which had been diluted beforehand such that each inoculation point comprised about $10^4$ colony-forming particles were used for the inoculation. The inoculation agar plates were incubated at 37° C. and the germ growth was read off after about 20 hours. The MIC value (μg/ml) indicated the lowest active compound concentration at which no growth was detectable with the naked eye.

The compounds according to the invention are distinguished in particular by the fact that they have lower interactions with mammalian DNA compared with the compounds according to the prior art. The $ID_{50}$ is understood as meaning the concentration of a substance at which DNA synthesis in cells from ovaries of the Chinese hamster (CHO-KI) is inhibited by 50%. This value is determined after incubation of the corresponding substances in decreasing dilution stages over defined periods of time. For this, the DNA synthesis in CHO-KI cells is determined in comparison with controls by means of fluorophotometric methods.

TABLE 1

MIC values (μg/ml) and $ID_{50}$ values of active compounds according to the invention

| | | Example | | | | | | | | | |
|---|---|---|---|---|---|---|---|---|---|---|---|
| Species | Strain | 1 | 2 | 3 | 5 | 6 | 18 | 19 | 20 | 21 | 22 |
| E. coli | Neumann | 0.125 | 0.015 | 0.015 | 0.015 | 0.06 | 0.03 | 0.03 | 0.03 | 0.015 | 0.125 |
| Staph. aureus | 133 | 0.062 | 0.015 | 0.015 | 0.015 | 0.015 | 0.015 | 0.015 | 0.015 | 0.015 | 0.031 |
| Staph. aureus | ICB 25701 | 8 | 0.062 | 0.031 | 0.031 | 0.125 | 0.25 | 0.06 | 0.125 | 0.125 | 2 |
| Ps. aeruginosa | Walter | 8 | 0.5 | 0.5 | 1 | 4 | 2 | 1 | 2 | 4 | 8 |
| Bac. fragilis | ES 25 | 16 | 0.5 | 0.125 | 0.125 | 0.25 | 1 | 0.125 | 1 | 0.125 | 4 |
| $ID_{50}$ (μg/ml) | | 24 | 1 | 4 | 8 | 10 | 1 | 4 | 16 | 10 | 8 |

TABLE 2

MIC values (μg/ml) and $ID_{50}$ values of active compounds from the prior art

| | | Examples from EP 520 240 | | | |
|---|---|---|---|---|---|
| | | 35 | | 36 | 7 |
| Species | Strain | Ref. 1 | Ref. 2 | Ref. 3 | Ref. 4 |
| E. coli | Neumann | 0.015 | 0.015 | 0.015 | 0.03 |
| Staph. aureus | 133 | 0.015 | 0.015 | 0.015 | 0.015 |
| Staph. aureus | ICB 25701 | 0.06 | 0.015 | 0.015 | — |
| Ps. aeruginosa | Walter | 0.5 | 1 | 0.5 | 1 |
| Bac. fragilis | ES 25 | 0.5 | 0.25 | 0.125 | 0.5 |
| $ID_{50}$ (μg/ml) | | 0.015 | 0.1 | 0.1 | 0.1 |

Ref. 1: 7-(4-amino-7-methyl-1,3,3a,4,7,7a-hexahydro-isoindol-2-yl)-1-cyclopropyl-6,8-difluoro-1,4-dihydro-4-oxo-3-quinolinecarboxylic acid,
Ref. 2: 7-(4-amino-7-methyl-1,3,3a,4,7,7a-hexahydro-isoindol-2-yl)-1-cyclopropyl-6-fluoro-1,4-dihydro-8-methoxy-4-oxo-3-quinolinecarboxylic acid, TABLE 2-continued MIC values (μg/ml) and $ID_{50}$ values of active compounds from the prior art

| | | Examples from EP 520 240 | | | |
|---|---|---|---|---|---|
| | | 35 | | 36 | 7 |
| Species | Strain | Ref. 1 | Ref. 2 | Ref. 3 | Ref. 4 |

Ref. 3: 7-(4-amino-7-methyl-1,3,3a,4,7,7a-hexahydro-isoindol-2-yl)-8-chloro-1-cyclopropyl-6-fluoro-1,4-dihydro-4-oxo-3-quinolinecarboxylic acid,
Ref. 4: 7-(7-methyl-4-methylamino-1,3,3a,4,7,7a-hexahydro-isoindol-2-yl)-8-chloro-1-cyclopropyl-6-fluoro-1,4-dihydro-4-oxo-3-quinolinecarboxylic acid.

Preparation of the intermediate products

EXAMPLE Z 1

A. 1-Methoxy-4-azatricyclo[5.2.2.0$^{2,6}$]undec-8-en-3,5-dione 11 g (0.1 mol) of 1-methoxycyclohexa-1,4-diene are heated under reflux with 0.1 g of tris(triphenylphosphine)-ruthenium dichloride and 8.8 g (0.09 mol) of maleimide in 100 ml of absolute chloroform overnight. The mixture is concentrated and the residue is recrystallized from 100 ml of toluene.

Yield 17.6 g (84.9% of theory),

Melting point: 159–161° C.

B. 1-Methoxy-4-azatricyclo[5.2.2.0$^{2,6}$]undec-8-ene 20.5 g (0.1 mol) of 1-methoxy-4-azatricyclo[5.2.2.0$^{2,6}$] undec-8-ene-3,5-dione in 100 ml of absolute tetrahydrofuran are added dropwise to 6 g of LiAlH$_4$ in 200 ml of absolute tetrahydrofuran and the mixture is stirred under reflux overnight. 6 ml each of water, 15% strength KOH solution and water again are added, the inorganic salts are filtered off with suction and boiled out twice with tetrahydrofuran, the filtrates are concentrated and the residue is distilled.

Yield: 12.3 g (68.6% of theory)

Boiling point: 100° C./0.04 mbar.

EXAMPLE Z 2

A. 1-Ethoxycarbonyl-4-azatricyclo[5.2.2.0$^{2,6}$]undec-8-ene-3,5-dione 13.5 g (0.138 mol) of maleimide and 25.3 g (0.17 mol) of ethyl 1,3-cyclohexadiene-1-carboxylate are heated under reflux with 1.4 g of 4-(tertbutyl)-pyrocatechol in 275 ml of toluene overnight. The mixture is concentrated and the residue is recrystallized from isopropanol.

Yield: 25.9 g (75% of theory)

Melting point: 172–173° C.

B. 1-Hydroxymethyl-4-azatricyclo[5.2.2.0-[5.2.2.0$^{2,6}$] undec-8-ene 12.5 g (50 mmol) of 1-ethoxycarbonyl-4-azatricyclo-[5.2.2.0$^{2,6}$]undec-8-ene-3,5-dione are reduced with LiAlH$_4$ as described under Z 1-B and the mixture is worked up accordingly.

Yield: 2.3 g (25.6% of theory)
Boiling point: 122–124° C./0.5 mbar.

EXAMPLE Z 3

A. 1-Dimethylamino-4-azatricyclo[5.2.2.0$^{2,6}$-]undec-8-ene-3,5-dione 9 g (73 mmol) of 1-dimethylaminocyclohexa-1,3-diene and 6.4 g (66 mmol) of maleimide are stirred in 100 ml of absolute dioxane at room temperature overnight. The mixture is concentrated and the residue is recrystallized from isopropanol.

Yield: 12 g (82.5% of theory)
Melting point: 170–172° C.

B. 1-Dimethylamino-4-azatricyclo[5.2.2.0$^{2,6}$]undec-8-ene 12 g (54.5 mmol) of 1-dimethylamino-4-azatricyclo-[5.2.2.0$^{2,6}$]undec-8-ene-3,5-dione are reduced with LiAlH$_4$ as described under Z 1-B and the mixture is worked up accordingly.

Yield 7.5 g (71.5% of theory)
Boiling point: 91–93° C./0.04 mbar.

EXAMPLE Z 4

A. 1-Cyano-4-azatricyclo[5.2.2.0$^{2,6}$]undec-8-ene-3,5-dione 59 g (0.56 mol) of 1-cyano-cyclohexa-1,3-diene are heated at 150° C. with 54 g (0.56 mol) of maleimide and 5 g of 4-(tert-butyl)-pyrocatechol in 1000 ml of dimethylformamide for 8 hours. The mixture is concentrated, the residue is stirred with water and toluene and the product which has crystallized is filtered off with suction, washed with isopropanol and dried in air.

Yield: 71 g (67.5% of theory)
Melting point: 213° C.

B. 1-Aminomethyl-4-azatricyclo[5.2.2.0$^{2,6}$]undec-8-ene 15.4 g (76.2 mmol) of 1-cyano-4-azatricyclo[5.2.2.0$^{2,6}$] undec-8-ene-3,5-dione are reduced with LiAlH$_4$ as described under Z 1-B and the mixture is worked up accordingly.

Yield: 7 g (51.5% of theory)
Boiling point: 97° C./0.1 mbar.

EXAMPLE Z 5

A. 4-azatricyclo[5.2.2.0$^{2,6}$]undec-8-ene-3,5-dione-1-carboxylic acid amide 41 g (0.203 mol) of 1-cyano-4-azatricyclo[5.2.2.0$^{2,6}$] undec-8-ene-3,5-dione are dissolved in 150 ml of 10% strength sodium hydroxide solution, and 130 ml of 30% strength H$_2$O$_2$ are added dropwise at 0° C. The mixture is stirred at 0° C. for 30 minutes and then at room temperature for 3 hours, the pH is brought to 4.5 with acetic acid and the product which crystallizes out is filtered off with suction.

Yield: 36.3 g (81% of theory)
Melting point: 158° C. (from isopropanol).

B. 1-Amino-4-azatricyclo[5.2.2.0$^{2,6}$]undec-8-ene-3,5-dione 74.5 g (0.338 mol) of 4-azatricyclo[5.2.2.0$^{2,6}$]undec-8-ene-3,5-dione-1-carboxylic acid amide are heated under reflux with 139 g (0.354 mol) of I-hydroxy-I-tosyloxy-iodobenzene in 1000 ml of acetonitrile for 3 hours. The mixture is cooled and the toluenesulphonic acid salt of the product which has crystallized out is filtered off with suction.

Yield: 112 g (95% of theory)
Melting point: 255–256° C.

The salt is suspended in 300 ml of water, and a solution of 12.5 g of NaOH in 40 ml of water is added. The salt dissolves rapidly, and after some time the product crystallizes out.

Yield: 43.5 g (70% of theory).

C. 1-Amino-4-azatricyclo[5.2.2.0$^{2,6}$]undec-8-ene 45 g (0.234 mol) of 1-amino-4-azatricyclo[5.2.2.0$^{2,6}$] undec-8-ene-3,5-dione are reduced with 24 g of LiAlH$_4$ in 500 ml of absolute dioxane as under Z 1-B and the mixture is worked up accordingly.

Yield: 14.8 g (40% of theory)
Boiling point: 95–105° C./0.08 mbar.

EXAMPLE Z 6

A. 4-Benzyl-1-cyano-4-azatricyclo[5.2.2.0$^{2,6}$]undec-8-ene-3,5-dione 39 g (0.35 mol) of 1-cyano-cyclohexa-1,3-diene are heated at 100° C. with 65.5 g (0.35 mol) of N-benzyl-maleimide in 700 ml of xylene for one hour and then under reflux for 1 hour. After cooling, the crystals are filtered off with suction and recrystallized from xylene.

Yield: 75 g (73.3% of theory)
Melting point: 175–177° C.

B. 1-Aminomethyl-4-benzyl-4-azatricyclo[5.2.2.0$^{2,6}$]undec-8-ene 14.6 g (50 mmol) of 4-benzyl-1-cyano-4-azatricyclo-[5.2.2.0$^{2,6}$]undec-8-ene-3,5-dione are reduced with 5 g of LiAlH$_4$ as described under Z 1-B and the mixture is worked up accordingly.

Yield: 6.4 g (47.7% of theory)
Boiling point: 158° C./0.1 mbar.

C. 1-Aminomethyl-4-azatricyclo[5.2.2.0$^{2,6}$]undecane 7.4 g (27.5 mmol) of 1-aminomethyl-4-benzyl-4-azatricyclo[5.2.2.0$^{2,6}$]undec-8-ene are hydrogenated in 100 ml of tetrahydrofuran using 1.5 g of palladium/active charcoal at 100° C./100 bar. The catalyst is filtered off with suction and the residue is distilled.

Yield: 3.1 g (62.5% of theory)
Boiling point: 89° C./0.1 mbar.

EXAMPLE Z 7

A. 4-Benzyl-4-azatricyclo[5.2.2.0$^{2,6}$]undec-8-ene-3,5-dione-1-carboxamide 14.5 g (50 mmol) of 4-benzyl-1-cyano-4-azatricyclo [5.2.2.0$^{2,6}$]undec-8-ene-3,5-dione are dissolved in 25 ml of methylene chloride, 2.5 g of tetrabutylammonium hydrogen sulphate and 17.5 ml of 20% strength sodium hydroxide solution are added, and 24 ml of 30% strength H$_2$O$_2$ are added dropwise at 0° C. The mixture is stirred at 0° C. for 30 minutes and then overnight at room temperature and diluted with methylene chloride, and the organic phase is separated off and washed with sodium chloride solution. It is dried over MgSO$_4$ and concentrated and the crystalline product is boiled up with xylene, any unreacted starting material dissolving. The product is filtered off hot with suction and dried in air.

Yield: 13 g (83.8% of theory)
Melting point: 224° C.

B. 1-Amino-4-benzyl-4-azatricyclo[5.2.2.0$^{2,6}$]undec-8-ene-3,5-dione 17.6 g (56.7 mmol) of 4-benzyl-4-azatricyclo[5.2.2.0$^{2,6}$] undec-8-ene-3,5-dione-1-carboxamide are reacted with 22.2 g of I-hydroxy-I-tosyloxy-iodobenzene as described under Z 5-B and the mixture is worked up accordingly.

Yield: 22.5 g (87% of theory) of the tosylate
Melting point: 222° C.

The free base is prepared from this as described under Z 5-B.

23

Yield: 12 g (86% of theory)

Melting point: 130–134° C.

C. 1-Amino-4-benzyl-4-azatricyclo[5.2.2.0$^{2,6}$]undec-8-ene 19.3 g (68.2 mmol) of 1-amino-4-benzyl-4-azatricyclo [5.2.2.0$^{2,6}$]undec-8-ene-3,5-dione are reduced with 8 g of LiAlH$_4$ as described under Z 1-B and the mixture is worked up accordingly.

Yield: 12.6 g (72.6% of theory)

Boiling point: 145–148° C./0.15 mbar

Melting point: 59–61° C.

D. 1-Amino-4-azatricyclo[5.2.2.0$^{2,6}$]undecane 8.3 g (32.6 mmol) of 1-amino-4-benzyl-4-azatricyclo [5.2.2.0$^{2,6}$]undec-8-ene are hydrogenated in 100 ml of ethanol over 1 g of palladium/active charcoal at 100° C./100 bar. The catalyst is filtered off with suction, the filtrate is concentrated and the residue is distilled.

Yield: 4.4 g (81.2% of theory)

Boiling point: 115° C./0.05 mbar.

EXAMPLE Z 8

A. Ethyl-4-benzyl-3,5-dioxo-4-azatricyclo[5.2.1.0$^{2,6}$]dec-8-ene-1-carboxylate 32.8 g (0.17 mol) of N-benzylmaleimide are heated under reflux with 24.2 g (0.17 mol) of diethyl tricyclo[5.2.1.0$^{2,6}$] deca-3,8-diene-1,4-dicarboxylate in 200 ml of 1,4-dioxane overnight. The mixture is concentrated, the residue is taken up in 80 ml of isopropanol and the product is allowed to crystallize out.

Yield: 23 g (41.6% of theory)

Melting point: 78–80° C.

B. 4-Benzyl-3,5-dioxo-4-azatricyclo[5.2.1.0$^{2,6}$]dec-8-ene-1-carboxylic acid 30 g (90 mmol) of ethyl 4-benzyl-3,5-dioxo-4-azatricyclo [5.2.1.0$^{2,6}$]dec-8-ene-1-carboxylate are heated under reflux with 5.3 g (0.13 mol) of NaOH in 150 ml of methanol overnight. The mixture is concentrated, the residue is taken up in 150 ml of water and the mixture is acidified with hydrochloric acid. The product which crystallizes out is filtered off with suction, washed with water and dried in air.

Yield: 23.5 g (87.8% of theory)

Melting point: 157° C.

C. 4-Benzyl-3,5-dioxo-4-azatricyclo[5.2.1.0$^{2,6}$]dec-8-ene-1-carboxylic acid amide 1.1 g (11 mmol) of triethylamine and then 1.15 g (12 mmol) of methyl chloroformate are added dropwise to 3 g (10 mmol) of 4-benzyl-3,5-dioxo-4-azatricyclo[5.2.1.0$^{2,6}$] dec-8-ene-1-carboxylic acid in 20 ml of absolute tetrahydrofuran at 0° C. The mixture is stirred at 0° C. for a further hour and the solution is poured onto 20 ml of ammonia solution. The mixture is stirred at room temperature for 1 hour and extracted several times with chloroform, and the extracts are dried over MgSO$_4$ and concentrated, whereupon the product crystallizes.

Yield: 1.78 g (60% of theory)

Melting point: 168° C.

Preparation of the active compounds

24

EXAMPLE 1

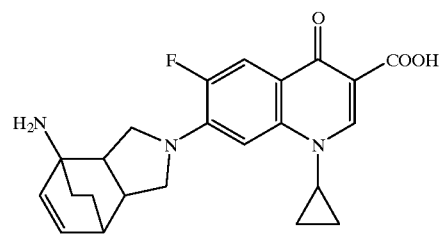

265 mg (1 mmol) of 1-cyclopropyl-6,7-difluoro-1,4-dihydro-4-oxo-3-quinolinecarboxylic acid are heated under reflux in a mixture of 4 ml of acetonitrile and 2 ml of dimethylformamide with 170 mg (1.5 mmol) of 1,4-diazabicyclo-[2.2.2]octane and 210 mg (1.1 mmol) of 86% pure 4-aza-tricyclo[5.2.2.0$^{2,6}$]undec-8-en-1-ylamine for 1 hour. The mixture is concentrated, the residue is stirred with 40 ml of water (pH=7) and the precipitate which has separated out is filtered off with suction, washed with water, and dried at 80° C. under a high vacuum.

Yield: 286 mg (70% of theory) of 7-(1-amino-4-aza-tricyclo[5.2.2.0$^{2,6}$]undec-8-en-4-yl)-1-cyclopropyl-6-fluoro-1,4-dihydro-4-oxo-3-quinolinecarboxylic acid, Melting point: 272–274° C. (with decomposition).

EXAMPLE 2

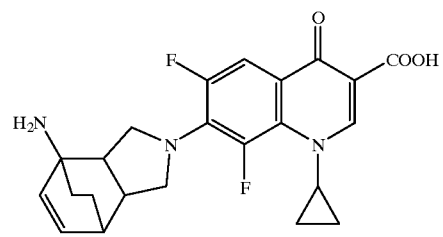

Under conditions corresponding to those in Example 1, 1-cyclopropyl-6,7,8-trifluoro-1,4-dihydro-4-oxo-3-quinolinecarboxylic acid gives 7-(1-amino-4-aza-tricyclo-5.2.2.0$^{2,6}$]undec-8-en-4-yl)-1-cyclopropyl-6,8-difluoro-1,4-dihydro-4-oxo-3-quinolinecarboxylic acid in a 61% yield, Melting point: 226–227° C. (with decomposition).

EXAMPLE 3

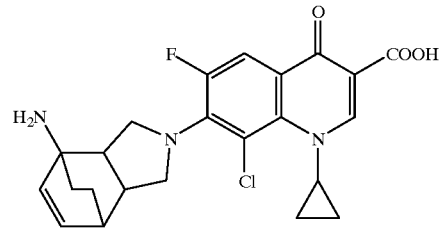

Under conditions corresponding to those in Example 1, 8-chloro-1-cyclopropyl-6,7-difluoro-1,4-dihydro-4-oxo-3-quinolinecarboxylic acid gives a crude product which is purified by chromatography over silica gel (mobile phase: methylene chloride/17% strength aqueous ammonia/methanol 30:8:1). 7-(1-Amino-4-aza-tricyclo[5.2.2.0$^{2,6}$]

undec-8-en-4-yl)-8-chloro-1-cyclopropyl-6-fluoro-1,4-dihydro-4-oxo-3-quinoline-carboxylic acid is obtained in a yield of 72%.

Melting point: 218–229° C. (with decomposition).

EXAMPLE 4

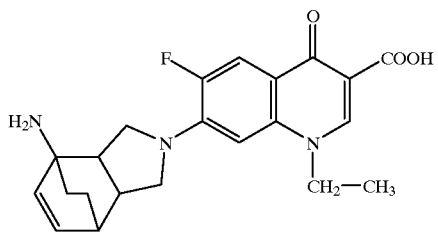

Under conditions corresponding to those in Example 1, 1-ethyl-6,7-difluoro-1,4-dihydro-4-oxo-3-quinolinecarboxylic acid gives a crude product which is purified by chromatography over silica gel (mobile phase: methylene chloride/17% strength aqueous ammonia/methanol 30:8:1). 7-(1-Amino-4-aza-tricyclo[5.2.2.0$^{2,6}$]undec-8-en-4-yl)-1-ethyl-6-fluoro-1,4-dihydro-4-oxo-3-quinolinecarboxylic acid, the melting point of which cannot be determined (sintering from 75° C.) is isolated in a yield of 53%.

$^1$H-NMR (CF$_3$COOD): δ6.41 d (1 H) and 6.63 ppm "t" (1 H).

EXAMPLE 5

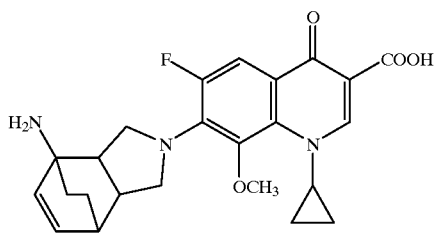

Under conditions corresponding to those in Example 1, 1-cyclopropyl-6,7-difluoro-1,4-dihydro-8-methoxy-4-oxo-3-quinolinecarboxylic acid gives 7-(1-amino-4-aza-tricyclo[5.2.2.0$^{2,6}$]undec-8-en-4-yl)-1-cyclopropyl-6-fluoro-1,4-dihydro-8-methoxy-4-oxo-3-quinolinecarboxylic acid in a yield of 64%.

Melting point: 224–225° C. (with decomposition).

EXAMPLE 6

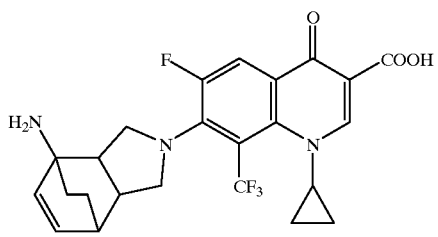

Under conditions corresponding to those in Example 1, 1-cyclopropyl-6,7-difluoro-1,4-dihydro-4-oxo-8-trifluoromethyl-3-quinolinecarboxylic acid gives a crude product which is purified by chromatography over silica gel (mobile phase: methylene chloride/17% strength aqueous ammonia/methanol 30:8;1). 7-(1-Amino-4-aza-tricyclo[5.2.2.0$^{2,6}$]undec-8-en-4-yl)-1-cyclopropyl-6-fluoro-1,4-dihydro-4-oxo-8-trifluoromethyl-3-quinolinecarboxylic acid is isolated in a yield of 32%.

Melting point: 163–166° C. (with decomposition).

EXAMPLE 7

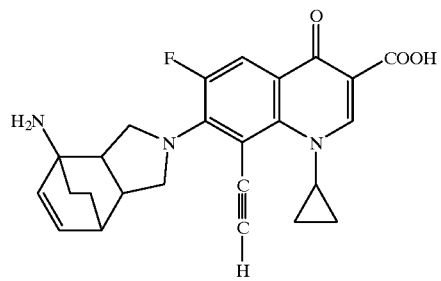

Under conditions corresponding to those in Example 1, 1-cyclopropyl-8-ethinyl-6,7-difluoro-1,4-dihydro-4-oxo-3-quinolinecarboxylic acid gives 7-(1-amino-4-aza-tricyclo[5.2.2.0$^{2,6}$]undec-8-en-4-yl)-1-cyclopropyl-8-ethinyl-6-fluoro-1,4-dihydro-4-oxo-3-quinolinecarboxylic acid, the melting point of which cannot be determined because of premature sintering from 107° C., in a yield of 87%.

$^1$H-NMR (CDCl$_3$): δ3.84 s (1 H), 6.03 d (1 H), 6.20 ppm dd (1 H).

EXAMPLE 8

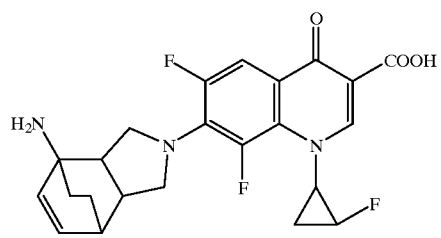

Under conditions corresponding to those in Example 1, 6,7,8-trifluoro-1-(cis-2-fluorocyclopropyl)-1,4-dihydro-4-oxo-3-quinolinecarboxylic acid gives a crude product which is purified by chromatography over silica gel (mobile phase: methylene chloride/17% strength aqueous ammonia/methanol 30:8:1). 7-(1-Amino-4-aza-tricyclo[5.2.2.0$^{2,6}$]undec-8-en-4-yl)-6,8-difluoro-1-(cis-2-fluorocyclopropyl)-1,4-dihydro-4-oxo-3-quinolinecarboxylic acid is isolated in a yield of 55%.

Melting point: 222–225° C. (with decomposition).

EXAMPLE 9

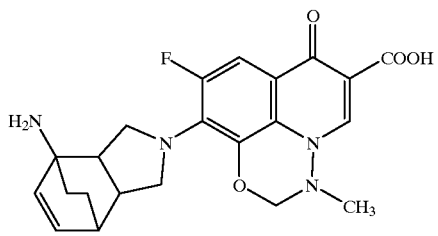

150 mg (0.53 mmol) of 9,10-difluoro-3-methyl-7-oxo-2,3-dihydro-7H-pyrido[1,2,3-d,e][1,3,4]-benzoxadiazine-6-carboxylic acid are heated at 110° C. with 130 mg (0.79 mmol) of 4-azatricyclo[5.2.2.0$^{2,6}$]undec-8-en-1-ylamine in 5 ml of pyridine under argon for 8 hours. The mixture is concentrated under a high vacuum and the residue is recrystallized from ethanol and dried.

Yield: 55 mg (24% of theory) of 10-(1-amino-4-azatricyclo[5.2.2.0$^{2,6}$]undec-8-en-4-yl)-9-fluoro-3-methyl-7-oxo-2,3-dihydro-7H-pyrido[1,2,3-d,e][1,3,4]benzoxadiazine-6-carboxylic acid, Melting point: 215–223° C. (with decomposition).

EXAMPLE 10

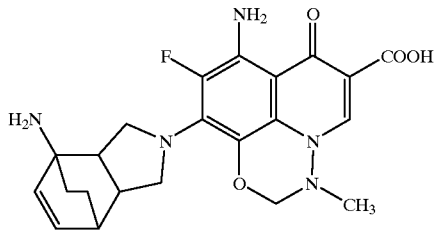

150 mg (0.51 mmol) of 8-amino-9,10-difluoro-3-methyl-7-oxo-2,3-dihydro-7H-pyrido[1,2,3-d,e][1,3,4]benzoxadiazine-6-carboxylic acid are heated at 120° C. with 125 mg (0.76 mmol) of 4-azatricyclo[5.2.2.0$^{2,6}$]undec-8-en-1-ylamine in 4.5 ml of dimethyl sulphoxide under argon for three hours. The mixture is concentrated under a high vacuum and the residue is recrystallized from ethanol and dried.

Yield: 190 mg (85% of theory) of 8-amino-10-(1-amino-4-azatricyclo[5.2.2.0$^{2,6}$]-undec-8-en-4-yl)-9-fluoro-3-methyl-7-oxo-2,3-dihydro-7H-pyrido[1,2,3-d,e][1,3,4]benzoxadiazine-6-carboxylic acid, Melting point: 230–239° C. (with decomposition).

EXAMPLE 11

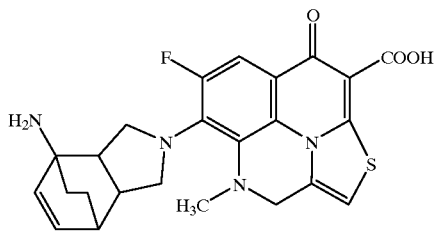

350 mg (1.086 mmol) of 7,8-difluoro-5-oxo-9,1-[(N-methylimino)methano]-5H-thiazolo-[3,2-a]-quinoline-4-carboxylic acid are heated at 120° C. with 267 mg (1.63 mmol) of 4-azatricyclo[5.2.2.0$^{2,6}$]undec-8-en-1-ylamine in 8 ml of dimethyl sulphoxide under argon for six hours. The mixture is concentrated under a high vacuum and the residue is recrystallized from ethanol and dried.

Yield: 330 mg (65% of theory) of 8-(1-amino-4-azatricyclo[5.2.2.0$^{2,6}$]undec-8-en-4-yl)-7-fluoro-5-oxo-9,1-[(N-methyl-imino)methano]-5H-thiazolo[3,2-a]quinoline-4-carboxylic acid, Melting point: >300° C.

EXAMPLE 12

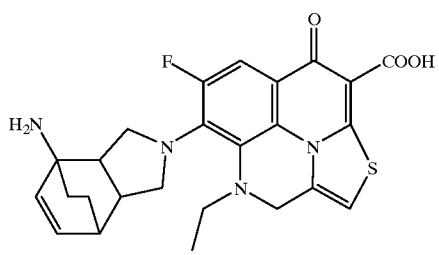

Analogously to Example 11, reaction with 7,8-difluoro-5-oxo-9,1-[(N-ethylimino)methano]-5H-thiazolo[3,2-a]quinoline-4-carboxylic acid gives 8-(1-amino-4-azatricyclo[5.2.2.0$^{2,6}$]undec-8-en-4-yl)-7-fluoro-5-oxo-9,1-[(N-ethyl-imino)methano]-5H-thiazolo[3,2-a]quinoline-4-carboxylic acid.

Melting point: >300° C.

EXAMPLE 13

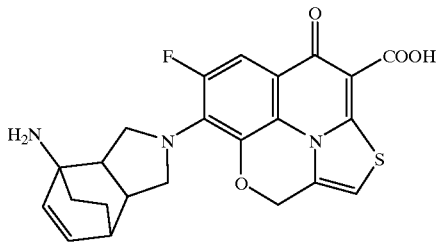

100 mg (0.323 mmol) of 7,8-difluoro-5-oxo-9,1-(epoxymethano)-5H-thiazolo[3,2-a]-quinoline-4-carboxylic acid are heated at 100° C. with 80 mg (0.49 mmol) of 4-azatricyclo[5.2.2.0$^{2,6}$]undec-8-en-1-ylamine in 3 ml of DMSO under argon for 2 hours. The mixture is concentrated under a high vacuum and the residue is recrystallized from ethanol and dried.

Yield: 114 mg (78% of theory) of 8-(1-amino-4-azatricyclo[5.2.2.0$^{2,6}$]undec-8-en-4-yl)-7-fluoro-5-oxo-9,1-(epoxymethano)-5H-thiazolo[3,2-a]quinoline-4-carboxylic acid, Melting point: 254–263° C.

EXAMPLE 14

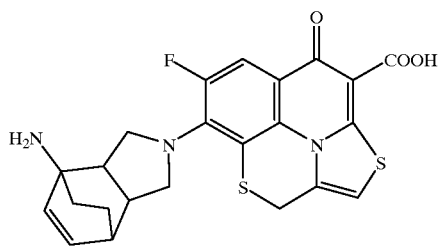

100 mg (0.307 mmol) of 7,8-difluoro-5-oxo-9,1-(epithiomethano)-5H-thiazolo[3,2-a]-quinoline-4-carboxylic acid are heated at 120° C. with 76 mg (0.46 mmol) of 1-amino-4-azatricyclo[5.2.2.0$^{2,6}$]undec-8-ene in 3 ml of DMSO under argon for four hours. The mixture is concentrated under a high vacuum and the residue is recrystallized from ethanol and dried.

Yield: 119 mg (83% of theory) of 8-(1-amino-4-azatricyclo[5.2.2.0$^{2,6}$]undec-8-en-4yl)- 7-fluoro-5-oxo-9,1-(epithiomethano)-5H-thiazolo[3,2-a]quinoline-4-carboxylic acid, Melting point: 285–290° C.

EXAMPLE 15

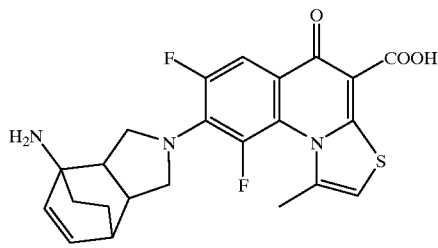

80 mg (0.245 mmol) of 7,8-difluoro-1-methyl-5-oxo-5H-thiazolo[3,2-a]-quinoline-4-carboxylic acid are heated at 80° C. with 46 mg (0.28 mmol) of 4-azatricyclo-[5.2.2.0$^{2,6}$]undec-8-en-1-ylamine in 3 ml of DMSO under argon for 3 hours. The mixture is concentrated under a high vacuum and the residue is recrystallized from ethanol and dried.

Yield: 41 mg (35% of theory) of 8-(1-amino-4-azatricyclo[5.2.2.0$^{2,6}$]-undec-8-en-4-yl)-7-fluoro-1-methyl-5-oxo-5H-thiazolo[3,2-a]-quinoline-4-carboxylic acid, Melting point: 122° C.

EXAMPLE 16

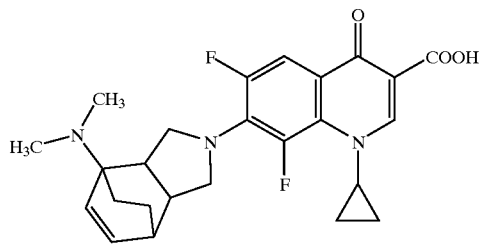

283 mg (1 mmol) of 1-cyclopropyl-6,7,8-trifluoro-1,4-dihydro-4-oxo-3-quinolinecarboxylic acid are heated under reflux in a mixture of 2 ml of acetonitrile and 1 ml of dimethylformamide with 224 mg (2 mmol) of 1,4-diazabicyclo[2.2.2]-octane and 210 mg (1.1 mmol) of (4-azatricyclo[5.2.2.0$^{2,6}$]undec-8-en-1-yl)-dimethylamine for 1 hour. The mixture is concentrated, the residue is stirred with water and the precipitate which has separated out is filtered off with suction, washed with water and dried at 100° C. under a high vacuum.

Yield: 360 mg (79% of theory) of 1-cyclopropyl-7-(1-dimethylamino-4-azatricyclo[5.2.2.0$^{2,6}$]undec-8-en-4-yl)-6,8-difluoro-1,4-dihydro-4-oxo-3-quinolinecarboxylic acid, Melting point: 238–240° C. (with decomposition).

EXAMPLE 17

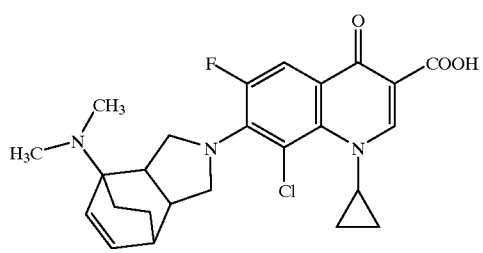

Under conditions corresponding to those in Example 16, 8-chloro-1-cyclopropyl-6,7-difluoro-1,4-dihydro-4-oxo-3-quinolinecarboxylic acid gives 8-chloro-1-cyclopropyl-7-(1-dimethylamino-4-azatricyclo[5.2.2.0$^{2,6}$]undec-8-en-4-yl)-6-fluoro-1,4-dihydro-4-oxo-3-quinolinecarboxylic acid in a yield of 65%, Melting point: 180–183° C. (with decomposition).

EXAMPLE 18

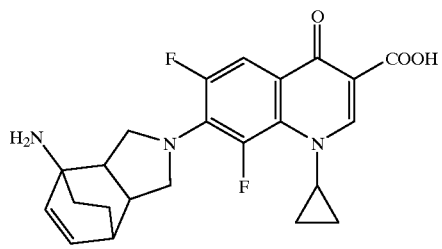

283 mg (1 mmol) of 1-cyclopropyl-6,7,8-trifluoro-1,4-dihydro-4-oxo-3-quinolinecarboxylic acid are heated under reflux in a mixture of 4 ml of acetonitrile and 2 ml of dimethylformamide with 224 mg (2 mmol) of 1,4-diazabicyclo-[2.2.2]octane and 191 mg (1.1 mmol) of 4-azatricyclo[5.2.2.0$^{2,6}$]undec-1-ylamine for 1 hour. The mixture is concentrated at 70° C./15 mbar, the residue is stirred with water and the precipitate which has separated out is filtered off with suction, washed with water and dried at 100° C. under a high vacuum.

Yield: 303 mg (73% of theory) of 7-(1-amino-4-azatricyclo[5.2.2.0$^{2,6}$]undec-4-yl)-1-cyclopropyl-6,8-difluoro-1,4-dihydro-4-oxo-3-quinolinecarboxylic acid, Melting point: 240–245° C. (with decomposition).

EXAMPLE 19

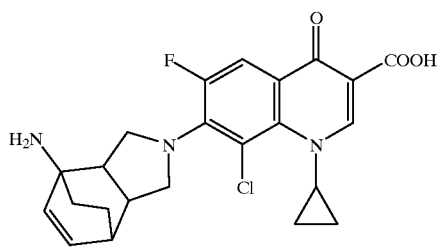

Under conditions corresponding to those in Example 18, 8-chloro-1-cyclopropyl-6,7-difluoro-1,4-dihydro-4-oxo-3-quinolinecarboxylic acid gives 7-(1-amino-4-azatricyclo-[5.2.2.0$^{2,6}$]undec-4-yl)-8-chloro-1-cyclopropyl-6-fluoro-1,4-dihydro-4-oxo-3-quinolinecarboxylic acid in a yield of 93%, Melting point: 232–235° C. (with decomposition).

EXAMPLE 20

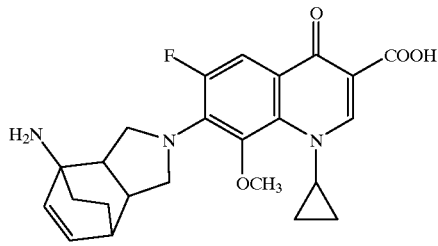

208 mg (2 mmol) of trimethyl borate, 123 mg (1.1 mmol) of 1,4-diazabicyclo[2.2.2]octane and 185 mg (1.1 mmol) of 4-aza-tricyclo[5.2.2.0$^{2,6}$]undec-1-ylamine are added to 295 mg (1 mmol) of 1-cyclopropyl-6,7-difluoro-1,4-dihydro-8-methoxy-4-oxo-3-quinolinecarboxylic acid in 3 ml of acetonitrile at room temperature and the mixture is then heated under reflux for 4 hours. The reaction mixture is concentrated at 80° C./20 mbar, the residue is stirred with water and the precipitate which has separated out is filtered off with suction, washed with water and dried at 100° C. under a high vacuum.

Yield: 218 mg (51% of theory) of 7-(1-amino-4-azatricyclo[5.2.2.0$^{2,6}$]undec-4-yl)-1-cyclopropyl-6-fluoro-1,4-dihydro-8-methoxy-4-oxo-3-quinolinecarboxylic acid, Melting point: 234–237° C. (with decomposition).

EXAMPLE 21

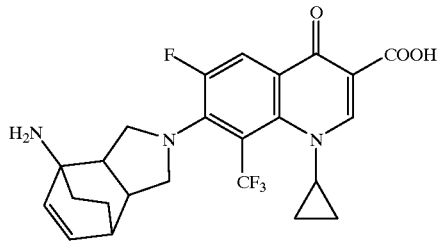

Under conditions corresponding to those in Example 18, 1-cyclopropyl-6,7-difluoro-1,4-dihydro-4-oxo-8-trifluoromethyl-3-quinolinecarboxylic acid gives a crude product, from which 7-(1-amino-4-azatricyclo[5.2.2.0$^{2,6}$]undec-4-yl)-1-cyclopropyl-6-fluoro-1,4-dihydro-4-oxo-8-trifluoromethyl-3-quinolinecarboxylic acid was isolated in a yield of 34% after purification by chromatography over silica gel (mobile phase: methylene chloride/17% strength aqueous ammonia/methanol 30:8:1).

Melting point: 211–215° C. (with decomposition).

EXAMPLE 22

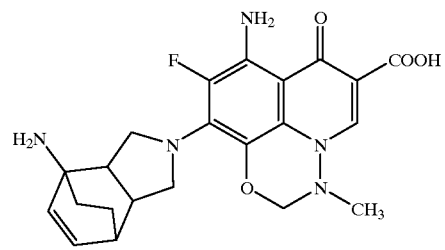

100 mg (0.336 mmol) of 8-amino-9,10-difluoro-3-methyl-7-oxo-2,3-dihydro-7H-pyrido[1,2,3-d,e][1,3,4] benzoxadiazine-6-carboxylic acid are heated at 120° C. with 111 mg (0.67 mmol) of 4-azatricyclo[5.2.2.0$^{2,6}$]undecan-1-ylamine in 3 ml of dimethyl sulphoxide under argon for 4 hours. The mixture is concentrated under a high vacuum and the residue is recrystallized from ethanol and dried.

Yield: 105 mg (70% of theory) of 8-amino-10-(1-amino-4-azatricyclo[5.2.2.0$^{2,6}$]undecan-4-yl)-9-fluoro-3-methyl-7-oxo-2,3-dihydro-7H-pyrido[1,2,3-d,e][1,3,4] benzoxadiazine-6-carboxylic acid, Melting point: 236° C.

EXAMPLE 23

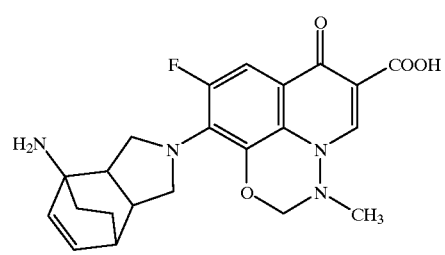

Analogously to Example 22, reaction with 9,10-difluoro-3-methyl-7-oxo-2,3-dihydro-7H-pyrido[1,2,3-d,e][1,3,4] benzoxadiazine-6-carboxylic acid gives 10-(1-amino-4-azatricyclo[5.2.2.0$^{2,6}$]undecan-4-yl)-9-fluoro-3-methyl-7-oxo-2,3-dihydro-7H-pyrido[1,2,3-d,e][1,3,4] benzoxadiazine-6-carboxylic acid.

Melting point: 143° C.

EXAMPLE 24

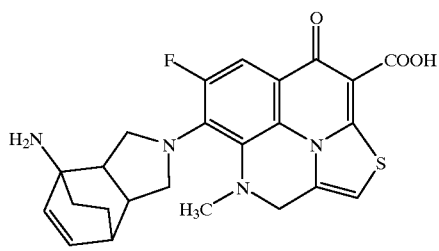

150 mg (0.465 mmol) of 7,8-difluoro-5-oxo-9,1-[(N-methylimino)methano]-5H-thiazolo[3,2-a]quinoline-4-carboxylic acid are heated at 130° C. with 153 mg (0.92 mmol) of 4-aza-tricyclo[5.2.2.0$^{2,6}$]undecan-1-yl in 3 ml of dimethyl sulphoxide under argon for 3 hours. The mixture is concentrated under a high vacuum and the residue is recrystallized from ethanol and dried.

Yield: 137 mg (63% of theory) of 8-(1-amino-4-azatricyclo[5.2.2.0$^{2,6}$]undecan-4-yl)-7-fluoro-5-oxo-9,1-[(N-methyl-imino)methano]-5H-thiazolo[3,2-a]quinoline-4-carboxylic acid, Melting point: >300° C.

EXAMPLE 25

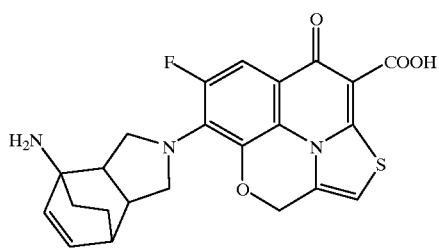

Analogously to Example 13, reaction with 1-amino-4-azatricyclo[5.2.2.0$^{2,6}$]undecane gives 8-(1-amino-4-azatricyclo[5.2.2.0$^{2,6}$]undecan-4-yl)-7-fluoro-5-oxo-9,1-(epoxymethano)-5H-thiazolo[3,2-a]quinoline-4-carboxylic acid.

Melting point: 270° C.

EXAMPLE 26

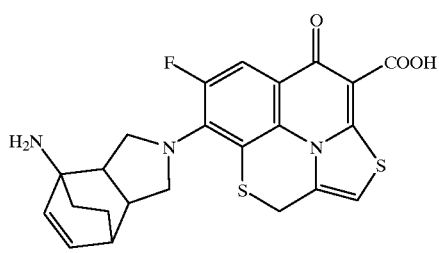

Analogously to Example 14, reaction with 1-amino-4-azatricyclo[5.2.2.0$^{2,6}$]undecane gives 8-(1-amino-4-azatricyclo[5.2.2.0$^{2,6}$]undecan-4-yl)-7-fluoro-5-oxo-9,1-(epithiomethano)-5H-thiazolo[3,2-a]quinoline-4-carboxylic acid.

Melting point: 270° C. (with decomposition).

EXAMPLE 27

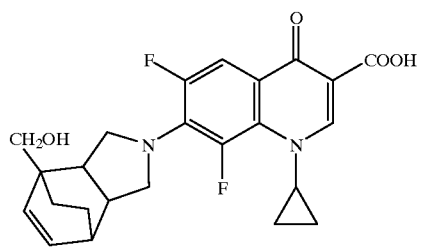

282 mg (1 mmol) of 1-cyclopropyl-6,7,8-trifluoro-1,4-dihydro-4-oxo-3-quinolinecarboxylic acid are heated under reflux in a mixture of 4 ml of acetonitrile and 2 ml of dimethylformamide with 224 mg (2 mmol) of 1,4-diazabicyclo[2.2.2]-octane and 200 mg (1.1 mmol) of (4-azatricyclo[5.2.2.0$^{2,6}$]undec-8-en-1-yl)-methanol for 1 hour. The precipitate which has separated out is filtered off with suction, washed with water and dried at 80° C. under a high vacuum.

Yield: 360 mg (81% of theory) of 1-cyclopropyl-6,8-difluoro-1,4-dihydro-7-(1-hydroxymethyl-4-azatricyclo [5.2.2.0$^{2,6}$]undec-8-en-4-yl)-4-oxo-3-quinolinecarboxylic acid, Melting point: 242–244° C. (with decomposition).

EXAMPLE 28

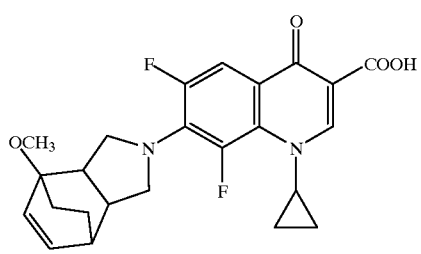

566 mg (2 mmol) of 1-cyclopropyl-6,7,8-trifluoro-1,4-dihydro-4-oxo-3-quinolinecarboxylic acid are heated under reflux in a mixture of 8 ml of acetonitrile and 4 ml of dimethylformamide with 350 mg (3.1 mmol) of 1,4-diazabicyclo[2.2.2]octane and 380 mg (2.1 mmol) of 1-methoxy-4-aza-tricyclo[5.2.2.0$^{2,6}$]undec-8-ene for 1 hour. The mixture is concentrated, the residue is stirred with 10 ml of water (pH=7) and the precipitate which has separated out is filtered off with suction, washed with water and dried at 90° C. under a high vacuum. 821 mg of a crude product which is recrystallized from glycol monomethyl ether, washed with ethanol and dried at 120° C. under a high vacuum are obtained.

Yield: 676 mg (76% of theory) of 1-cyclopropyl-6,8-difluoro-1,4-dihydro-7-(1-methoxy-4-azatricyclo[5.2.2.0$^{2,6}$]undec-8-en-4-yl)-4-oxo-3-quinolinecarboxylic acid, Melting point: 183–185° C. (with decomposition).

EXAMPLE 29

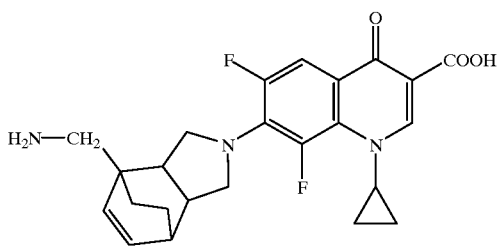

Under conditions corresponding to those in Example 18, (4-azatricyclo[5.2.2.0$^{2,6}$]undec-8-en-1-ylmethyl)amine gives, after recrystallization from glycol monomethyl ether, 7-(1-aminomethyl-4-azatricyclo[5.2.2.0$^{2,6}$]undec-8-en-4-yl)-1-cyclopropyl-6,8-difluoro-1,4-dihydro-4-oxo-3-quinolinecarboxylic acid in a yield of 59%, Melting point: 238–240° C. (with decomposition).

EXAMPLE 30

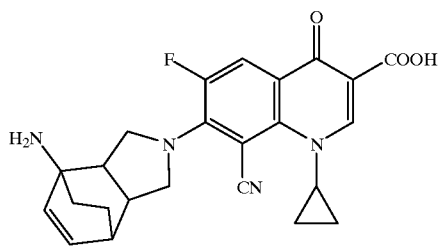

In accordance with Example 1, 8-cyano-1-cyclopropyl-7-chloro-6-fluoro-1,4-dihydro-4-oxo-3-quinolinecarboxylic acid is employed and the mixture is heated at 80° C. for 8 hours. After concentration and working up with ethanol, 7-(1-amino-4-azatricyclo[5.2.2.0$^{2,6}$]undec-8-en-4-yl)-8-cyano-1-cyclopropyl-6-fluoro-1,4-dihydro-4-oxo-3-quinolinecarboxylic acid is obtained in a yield of 51%, Melting point: 180–182° C. (with decomposition).

EXAMPLE 31

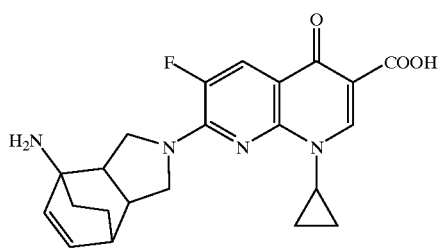

290 mg (≈1.5 mmol) of 86% pure 4-aza-tricyclo[5.2.2.0$^{2,6}$]undec-8-en-1-ylamine are added to 283 mg (1 mmol) of 7-chloro-1-cyclopropyl-6-fluoro-1,4-dihydro-4-oxo-1,8-naphthyridine-3-carboxylic acid in 6 ml of acetonitrile at 25° C. and the mixture is stirred at 25° C. for 1 hour. The precipitate is filtered off with suction, washed with ethanol, dried at 60° C./0.1 mbar (crude yield: 398 mg) and purified by chromatography (silica gel, methylene chloride/17% strength aqueous ammonia/methanol 30:8:1).

Yield: 171 mg (42% of theory) of 7-(1-amino-4-azatricyclo[5.2.2.0$^{2,6}$]undec-8-en-4-yl)-1-cyclopropyl-6-fluoro-1,4-dihydro-4-oxo-1,8-naphthyridine-3-carboxylic acid, Melting point: 308–311° C. (with decomposition).

EXAMPLE 32

A

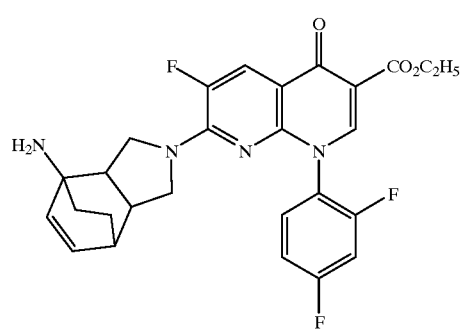

B

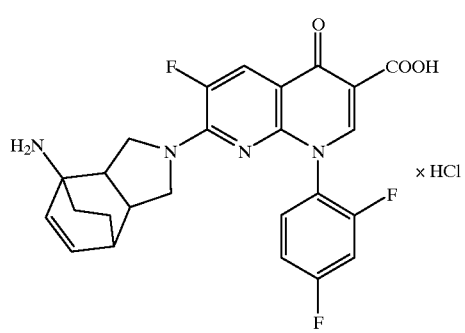

× HCl

A. Analogously to Example 31, the reaction is carried out with ethyl 7-chloro-6-fluoro-1-(2,4-difluorophenyl)-1,4-dihydro-4-oxo-1,8-naphthyridine-3-carboxylate to give ethyl 7-(1-amino-4-azatricyclo[5.2.2.0$^{2,6}$]undec-8-en-4-yl)-6-fluoro-1-(2,4-difluorophenyl)-1,4-dihydro-4-oxo-1,8-naphthyridine-3-carboxylate in a yield of 41%, Melting point: 210–213° C. (with decomposition).

B. 170 mg (0.33 mmol) of ethyl 7-(1-amino-4-azatricyclo[5.2.2.0$^{2,6}$]undec-8-en-4-yl)-6-fluoro-1-(2,4-difluorophenyl)-1,4-dihydro-4-oxo-1,8-naphthyridine-3-carboxylate are heated under reflux in a mixture of 2 ml of acetic acid and 1.5 ml of half-concentrated hydrochloric acid for 2 hours. The solution is concentrated, the residue is stirred with a little water and the precipitate is filter off with suction.

Yield: 150 mg (92% of theory) of 7-(1-amino-4-azatricyclo[5.2.2.0$^{2,6}$]undec-8-en-4-yl)-6-fluoro-1-(2,4-difluorophenyl)-1,4-dihydro-4-oxo-1,8-naphthyridine-3-carboxylic acid hydrochloride, Melting point: 270–272° C. (with decomposition).

EXAMPLE 33

Under conditions corresponding to those in Example 1, 6,7-difluoro-1-(2,4-difluorophenyl)-1,4-dihydro-5-methyl-4-oxo-3-quinolinecarboxylic acid gives a crude product which is purified by chromatography on silica gel (mobile phase: methylene chloride/17% strength aqueous ammonia/methanol 30:8:1). 7-(1-Amino-4-azatricyclo[5.2.2.0$^{2,6}$]undec-8-en-4-yl)-6-fluoro-1-(2,4-difluorophenyl)-1,4-dihydro-5-methyl-4-oxo-3-quinolinecarboxylic acid is isolated in a yield of 91%, Melting point: 281–283° C. (with decomposition).

EXAMPLE 34

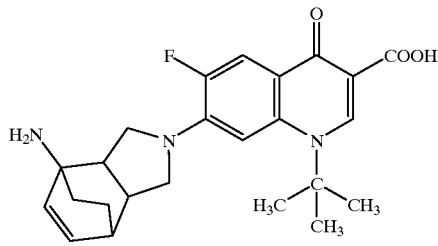

Under conditions corresponding to those in Example 1, 1-tert-butyl-6,7-difluoro-1,4-dihydro-4-oxo-3-quinolinecarboxylic acid gives 7-(1-amino-4-aza-tricyclo[5.2.2.0$^{2,6}$]undec-8-en-4-yl)-1-tert-butyl-6-fluoro-1,4-dihydro-4-oxo-3-quinolinecarboxylic acid in a yield of 61%, Melting point: 263–265° C. (with decomposition).

We claim:
1. A compound of the formula (I)

$$T—Q \qquad (I)$$

in which

Q denotes a radical of the formulae

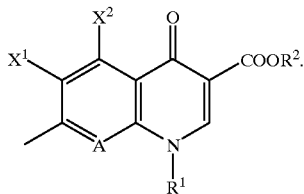

wherein
$R^2$ represents hydrogen, alkyl which has 1 to 3 carbon atoms and is optionally substituted by hydroxyl, methoxy, amino or dimethylamino, benzyl, (5-methyl-2-oxo-1,3-dioxol-4-yl)-methyl, acetoxymethyl, pivaloyloxymethyl, 5-indanyl, phthalidinyl or 3-acetoxy-2-oxo-butyl,
$X^1$ represents halogen or nitro,
$X^2$ represents hydrogen, halogen, amino, hydroxyl, methoxy, mercapto, methyl, halogenomethyl or vinyl,
A represents C—$R^7$, wherein
$R^7$ together with $R^1$ forms a bridge having the structure —*O—CH$_2$—CH—CH$_3$, —*S—CH$_2$—CH$_2$—, —*S—CH$_2$—CH—CH$_3$, —*S—CH$_2$—CH—CH$_2$F, —*CH$_2$—CH$_2$—CH—CH$_3$ or —*O—CH$_2$—N—R$^8$, wherein the atom labelled with * is linked to the carbon atom of A and wherein
$R^8$ denotes hydrogen, methyl or formyl, and T denotes a radical of the formula

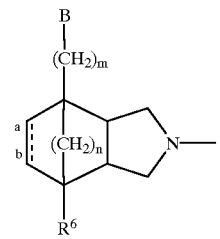

wherein
B represents NR$^3$R$^4$ or OR$^5$, wherein
$R^3$ represents hydrogen, methyl or alkoxycarbonyl having 1 to 4 carbon atoms in the alkyl part,
$R^4$ represents hydrogen or methyl and
$R^5$ represents hydrogen or methyl,
$R^6$ represents hydrogen or methyl,
m represents 0 or 1 and
n represents 1 or 2,
and wherein a single or a double bond can stand between the carbon atoms a and b,
or the pharmaceutically usable hydrate or acid addition salt thereof, or the alkali metal, alkaline earth metal, silver or guanidinium salt of the underlying carboxylic acid.

2. A compound of the formula (I) according to claim 1, in which
Q and T have the abovementioned meaning and
$R^2$ represents hydrogen, alkyl having 1 to 2 carbon atoms, benzyl or (5-methyl-2-oxo-1,3-dioxol-4-yl)-methyl,
$X^1$ represents fluorine or chlorine,
$X^2$ represents hydrogen, halogen, amino, methyl, trifluoromethyl or vinyl,
A represents C—$R^7$, wherein
$R^7$ together with $R^1$ forms a bridge having the structure —*O—CH$_2$—CH—CH$_3$, —*S—CH$_2$—CH$_2$—, —*CH$_2$—CH$_2$—CH—CH$_3$ or —*O—CH$_2$—N—R$^8$, wherein the atom labelled with * as linked to the carbon atom of A, and wherein
$R^8$ denotes hydrogen or methyl, and
B represents NR$^3$R$^4$ or OR$^5$, wherein
$R^3$ represents hydrogen, methyl or alkoxycarbonyl having 1 to 4 carbon atoms in the alkyl part,
$R^4$ represents hydrogen or methyl and
$R^5$ represents hydrogen or methyl,
$R^6$ represents hydrogen or methyl,
m represents 0 or 1 and
n represents 1 or 2,
wherein a single or a double bond can stand between the carbon atoms a and b,
or the pharmaceutically usable hydrate or acid addition salt thereof, or the alkali metal, alkaline earth metal, silver or guanidinium salt of the underlying carboxylic acid.

3. A compound of the formula (I) according to claim 1, in which
Q and T have the abovementioned meaning and in which
$R^2$ represents hydrogen, alkyl having 1 to 2 carbon atoms or (5-methyl-2-oxo-1,3-dioxol-4-yl)-methyl,
$X^1$ represents fluorine,
$X^2$ represents hydrogen, fluorine, amino, methyl or vinyl,
A C—$R^7$, wherein
$R^7$ together with $R^1$ forms a bridge having the structure —*O—CH$_2$—CH—CH$_3$ or —*O—CH$_2$—N—R$^8$, where the atom labelled with * is linked to the carbon atom of A, and wherein $R^8$ denotes hydrogen or methyl, and B represents $NR^3R^4$ or $OR^5$, wherein $R^3$ represents hydrogen or methyl, $R^4$ represents hydrogen or methyl and $R^5$ represents hydrogen or methyl, $R^6$ represents hydrogen, m represents 0 or 1 and n represents 1 or 2, wherein a single or a double bond can stand between the carbon atoms a and b, or the pharmaceutically usable hydrate or acid addition salt thereof, or the alkali metal, alkaline earth metal, silver or guanidinium salt of the underlying carboxylic acid.

4. Diastereomerically pure and enantiomerically pure compounds according to claim 1.

5. An antibacterial composition comprising an antibacterially effective amount of a compound or addition product thereof according to claim 1 and a diluent.

6. A composition according to claim 5 in the form of a tablet, capsule or ampule.

7. A composition according to claim 5, wherein the diluent comprises an animal feed stock.

8. A method of combating bacteria in a patient in need thereof which comprises administering to such patient an antibacterially effective amount of a compound or addition product thereof according to claim 1.

9. A method of promoting the growth of an animal which comprises administering to said animal a growth promoting effective amount of a compound or addition product thereof according to claim 1.

* * * * *